(12) United States Patent
Miesel et al.

(10) Patent No.: US 8,021,299 B2
(45) Date of Patent: Sep. 20, 2011

(54) CORRELATING A NON-POLYSOMNOGRAPHIC PHYSIOLOGICAL PARAMETER SET WITH SLEEP STATES

(75) Inventors: Keith A. Miesel, St. Paul, MN (US); Kenneth T. Heruth, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 735 days.

(21) Appl. No.: 11/410,448

(22) Filed: Apr. 25, 2006

(65) Prior Publication Data

US 2007/0015976 A1 Jan. 18, 2007

Related U.S. Application Data

(60) Provisional application No. 60/686,317, filed on Jun. 1, 2005.

(51) Int. Cl.
*A61B 5/04* (2006.01)
(52) U.S. Cl. .......................... 600/301; 128/920
(58) Field of Classification Search .................. None
See application file for complete search history.

(56) References Cited

U.S. PATENT DOCUMENTS

| | | | |
|---|---|---|---|
| 4,297,685 A | 10/1981 | Brainard, II | |
| 4,550,736 A | 11/1985 | Broughton et al. | |
| 4,771,780 A | 9/1988 | Sholder | |
| 4,776,345 A | 10/1988 | Cohen et al. | |
| 4,846,195 A | 7/1989 | Alt | |
| 5,040,536 A | 8/1991 | Riff | |
| 5,058,584 A | 10/1991 | Bourgeois | |
| 5,125,412 A | 6/1992 | Thornton | |
| 5,154,180 A | 10/1992 | Blanchet et al. | |
| 5,233,984 A | 8/1993 | Thompson | |
| 5,275,159 A * | 1/1994 | Griebel | 600/324 |
| 5,299,118 A * | 3/1994 | Martens et al. | 600/509 |
| 5,335,657 A | 8/1994 | Terry, Jr. et al. | |
| 5,337,758 A | 8/1994 | Moore et al. | |

(Continued)

FOREIGN PATENT DOCUMENTS

DE 198 31 109 1/2000

(Continued)

OTHER PUBLICATIONS

Itamar Medical Information, http://itamar-medical.com/content.asp?id-id=31, 2 pgs. Jan. 31, 2005. Provided by Applicant in IDS dated Mar. 8, 2007.*

(Continued)

*Primary Examiner* — Sam Yao
*Assistant Examiner* — Bobby Soriano
(74) *Attorney, Agent, or Firm* — Shumaker & Sieffert, P.A.

(57) ABSTRACT

Values of a non-polysomnographic (non-PSG) physiological parameter set may be correlated to polysomnographically (PSG) determined sleep states. The correlated values of the non-PSG parameter set and sleep states may be analyzed, and a relationship between the values and sleep states may be determined. The relationship may allow determination of sleep states for any given patient based on values of the non-PSG physiological parameter set for the patient. The non-PSG physiological parameter set does not include physiological parameters typically required for PSG, such as brain electrical activity (EEG), eye movement (EOG), and jaw or neck muscular activity or tone (EMG). Medical devices, such as implantable medical devices (IMDs) that would generally be unable to monitor such physiological parameters, may apply the relationship to values of the non-PSG physiological parameter set for a patient to identify sleep states of the patient.

36 Claims, 8 Drawing Sheets

U.S. PATENT DOCUMENTS

| | | |
|---|---|---|
| 5,342,409 A | 8/1994 | Mullett |
| 5,469,861 A | 11/1995 | Piscopo et al. |
| 5,476,483 A | 12/1995 | Bornzin et al. |
| 5,514,162 A | 5/1996 | Bornzin et al. |
| 5,593,431 A | 1/1997 | Sheldon |
| 5,622,428 A | 4/1997 | Bonnet |
| 5,645,053 A | 7/1997 | Remmers et al. |
| 5,732,696 A | 3/1998 | Rapoport et al. |
| 5,782,884 A | 7/1998 | Stotts et al. |
| 5,851,193 A * | 12/1998 | Arikka et al. ............ 600/595 |
| 5,895,371 A | 4/1999 | Levitas et al. |
| 5,904,708 A | 5/1999 | Goedeke |
| 5,919,149 A | 7/1999 | Allum |
| 5,941,906 A | 8/1999 | Barreras, Sr. et al. |
| 5,944,680 A | 8/1999 | Christopherson et al. |
| 5,999,846 A | 12/1999 | Pardey et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,165,143 A | 12/2000 | van Lummel |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,416,471 B1 | 7/2002 | Kumar et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,605,038 B1 | 8/2003 | Teller et al. |
| 6,611,783 B2 | 8/2003 | Kelly, Jr. et al. |
| 6,659,968 B1 | 12/2003 | McClure |
| 6,687,538 B1 | 2/2004 | Hrdlicka et al. |
| 6,731,984 B2 | 5/2004 | Cho et al. |
| 6,752,766 B2 | 6/2004 | Kowallik et al. |
| 6,773,404 B2 | 8/2004 | Poezevera et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,928,324 B2 | 8/2005 | Park et al. |
| 6,964,641 B2 | 11/2005 | Cho et al. |
| 7,162,304 B1 | 1/2007 | Bradley |
| 2001/0031930 A1 | 10/2001 | Roizen et al. |
| 2001/0037067 A1 | 11/2001 | Tchou et al. |
| 2002/0019586 A1* | 2/2002 | Teller et al. ............ 600/300 |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0102814 A1 | 5/2004 | Sorensen et al. |
| 2004/0111040 A1 | 6/2004 | Ni et al. |
| 2004/0111041 A1* | 6/2004 | Ni et al. ............ 600/544 |
| 2005/0042589 A1* | 2/2005 | Hatlestad et al. ............ 434/262 |
| 2005/0085738 A1* | 4/2005 | Stahmann et al. ............ 600/529 |
| 2005/0113710 A1 | 5/2005 | Stahmann et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245988 A1 | 11/2005 | Miesel |

FOREIGN PATENT DOCUMENTS

| | | |
|---|---|---|
| DE | 100 24 103 | 11/2001 |
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| GB | 2 330 912 A | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |
| WO | WO 2005/028029 | 3/2005 |
| WO | WO 2005/035050 | 4/2005 |

OTHER PUBLICATIONS

Amzica, "Physiology of Sleep and Wakefulness as it Relates to the Physiology of Epilepsy," Journal of Clinical Neurophysiology, American Clinical Neurophysiology Society, 19(6), pp. 488-503, (2002).

Dinner, "Effect of Sleep on Epilepsy," Journal of Clinical Neurophysiology, American Clinical Neurophysiology Society, 19(6), pp. 504-513, (2002).

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).

Mendez et al. "Interactions Between Sleep and Epilepsy," Journal of Clinical Neurophysiology, American Clinical Neurophysiology Society, 18(2), pp. 106-127, (2001).

"MiniMitter® Physiological and Behavioral Monitoring for Humans and Animals," http://www.minimitter.com/Products/Actiwatch, 3 pgs., Feb. 20, 2006.

"IBM & Citzen Watch develop Linux-based 'WatchPad'," 5 pgs., http://www.linuxdevices.com/news/NS6580187845.html, Feb. 20, 2006.

"Design Competition: Runners-Up for the Best Three Designs," EPN, vol. 26, No. 1, 1 pg., (2002).

"Watch," Wikipedia, the free encyclopedia, 6 pgs., http://en.wikipedia.org/wiki/Watch, Feb. 20, 2006.

Kassam, "2005 EDP Topic 'MK4': Tremor Data-Logger for Parkinson's Disease Patients," http://www.ee.ryerson.ca/~courses/edp2005/MK4.html, 3 pgs., Feb. 20, 2006.

Tuisku, "Motor Activity Measured by Actometry in Neuropsychiatric Disorders," Department of Psychiatry, University of Helsinki, Helsinki, Finland, 115 pgs. (2002).

Smith et al., "Presleep Cognitions in Patients with Insomnia Secondary to Chronic Pain," Journal of Behavioral Medicine, vol. 24, No. 1, pp. 93-114, (2001).

Smith et al. "How do sleep disturbance and chronic pain inter-relate? Insights from the longitudinal and cognitive-behavioral clinical trials literature," Sleep Medicine Reviews, YSMRV 286, pp. 1-14, (2003).

Goodrich et al., "The Prediction of Pain Using Measures of Sleep Quality," Pain Digest, 8:23-25, (1998).

"Analysis of heart rate dynamics by methods derived from nonlinear mathematics: Clinical applicability and prognostic significance" http:/herkules.oulu.fi.isbn9514250133/html, 4 pgs., (2004).

Kerr et al., "Analysis of the sit-stand-sit movement cycle in normal subjects," Clinical Biomechanics, vol. 12, No. 4, pp. 236-245, (1997).

International Search Report and the Written Opinion dated Aug. 25, 2006 for corresponding PCT/US2006/015369, filed Apr. 25, 2006 (11 pgs.).

Aminian et al. "Physical Activity Monitoring Based on Accelerometry: Validation and Comparison with Video Observation," Medical & Biological Engineering & Computing, vol. 37, No. 2, pp. 304-308 (1999).

Medcare—A Global Leader in Sleep Diagnostics, Embletta Recording System, http://www.medcare.com/products/diagnostic/embletta/, 2 pgs. Jan. 31, 2005.

Medcare—A Global Leader in Sleep Diagnostics, Somnologica for Embletta, http://www.medcare.com/products/diagnostic/embletta/SomnoEmbletta/index.asp, 1 pg. Jan. 31, 2005.

MAP Medizin-Technologie GmbH, Poly-MESAM®, http://195.244.124.130/map/de/eng/map_med.nsf/smsall/70564A3FCBE4188AC1256EF4.., 4 pgs. Jan. 31, 2005.

Merlin, http://www.aha.ru/~pir/english/merlin/, 4 pgs. Jan. 31, 2005.

Sleep Solutions—PR Newswire: Sleep Solutions Introduces NovaSom™ QSG™ for PSG . . . , http://www.sleep-solutions.com/press_room/novasom.htm, 2 pgs. Jan. 31, 2005.

Itamar Medical Information, http://itamar-medical.com/content.asp?id-id=31, 2 pgs. Jan. 31, 2005.

Criticare System Inc.,—504DX Portable Pulse Oximeter, http://www.csiusa.com/504dx.html, 4 pgs. Jan. 31, 2005.

Snap® Laboratories, Product Fact Sheet, http://www.snaplab.com/mp_fact.htm, 2 pgs. Jan. 31, 2005.

Sleep Strip & Bite Strip, http://ww.quietsleep.com/snoringapnea/sleepstrip.htm, 8 pgs. Jan. 31, 2005.

"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.

"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.

"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.

Notification of Transmittal of the International Preliminary Report on Patentability, dated Sep. 26, 2007 for corresponding PCT Application No. PCT/US2006/015369 (11 pgs.).

* cited by examiner

CORRELATING A NON-POLYSOMNOGRAPHIC PHYSIOLOGICAL PARAMETER SET WITH SLEEP STATES

This application claims the benefit of U.S. provisional application No. 60/686,317, filed Jun. 1, 2005, the entire content of which is incorporated herein by reference.

TECHNICAL FIELD

The invention relates to medical devices and, more particularly, to medical devices that monitor physiological parameters.

BACKGROUND

The ability to determine the sleep state of a patient, e.g., whether or not a patient is asleep, or whether a sleeping patient is within the rapid eye movement (REM), or one of the nonrapid eye movement (NREM) states (S1, S2, S3, S4), is useful in a variety of medical contexts. In some situations, the ability to determine the sleep state of a patient is used to diagnose conditions of the patient. For example, the amount of time that patients sleep or are within the various sleep states during sleep, the extent of arousals during sleep, and the times of day that patients sleep have been used to diagnose sleep apnea. Such sleep information could also be used to diagnose psychological disorders, such as depression and mania.

In other situations, a determination as to whether a patient is asleep is used to control delivery of therapy to the patient by a medical device, such as an implantable medical device (IMD). For example, neurostimulation or drug therapies can be suspended when the patient is asleep, or the intensity/dosage of the therapies can be reduced when a patient is asleep. As another example, the rate response settings of a cardiac pacemaker may be adjusted to less aggressive settings when the patient is asleep so that the patient's heart will not be paced at an inappropriately high rate during sleep. In these examples, therapy may be suspended or adjusted when the patient is asleep to avoid patient discomfort, or to reduce power consumption and/or conserve the contents of a fluid reservoir of an IMD when the therapy may be unneeded or ineffective. However, in other cases, a therapy intended to be delivered when the patient is asleep, such as therapy intended to prevent or treat sleep apnea, is delivered based on a determination that the patient is asleep.

In some cases, an ailment may affect the quality of a patient's sleep. For example, chronic pain may cause a patient to have difficulty falling asleep, disturb the patient's sleep, e.g., cause the patient to wake, and prevent the patient from achieving deeper sleep states, such as one or more of the NREM sleep states. Other ailments that may negatively affect patient sleep quality include movement disorders and congestive heart failure.

Further, in some cases, poor sleep quality may increase the symptoms experienced by a patient due to an ailment. For example, poor sleep quality has been linked to increased pain symptoms in chronic pain patients. The link between poor sleep quality and increased symptoms is not limited to ailments that negatively impact sleep quality, such as those listed above. Nonetheless, the condition of a patient with such an ailment may progressively worsen when symptoms disturb sleep quality, which in turn increases the frequency and/or intensity of symptoms. The increased symptoms may, in turn, further disturb sleep quality.

Because of the relationship between quality of sleep and symptoms, the quality of a patient's sleep may be indicative of the progression of an ailment and/or the effectiveness of a therapy delivered to treat the ailment. Assessing the quality of a patient's sleep in order to evaluate the progression of an ailment or the effectiveness of a therapy delivered to treat the ailment may involve identifying sleep states to, for example, identify disturbances in sleep, or difficulty in achieving or maintaining deeper sleep states. Consequently, it may be desirable for a medical device, such as an IMD, that treats the ailment of the patient to identify sleep states of patient.

The "gold standard" for identifying sleep states of a patient is polysomnography (PSG). PSG involves monitoring the electroencephalogram (EEG) of the patient over an extended period of time, e.g., overnight when the patient is attempting to sleep. Often, PSG also involves monitoring one or both of an electrooculogram (EOG) and a chin or jaw electromyogram (EMG) during the extended period of time. In some cases, PSG may additionally involve monitoring other physiological parameters of the patient, such as heart rate, respiration rate, and blood oxygen saturation level.

However, PSG is typically conducted in a clinical setting over the course of one night utilizing multiple sensors applied to a patient and coupled to a recording system. A technician or algorithm analyzes or "scores" the recorded sensor data to identify the sleep states of the subject during the night. Because EEG, EOG, and chin or jaw EMG monitoring typically require that an array of obtrusive external electrodes be placed on a patient's scalp and face and coupled to an external monitoring device, PSG is generally unsuitable for long-term monitoring of a patient's sleep states by a medical device, and particularly an IMD, as would be desired for identification of sleep states to control delivery of therapy or monitor the quality of a patient's sleep.

SUMMARY

In general, the invention is directed to techniques for correlating values of a non-polysomnographic (non-PSG) physiological parameter set to sleep states. The non-PSG physiological parameter set may include, for example, one or more of posture, activity level, heart rate, electrocardiogram (ECG) morphology, respiration rate, respiratory volume, blood pressure, blood oxygen saturation, core temperature, partial pressure of oxygen within blood, partial pressure of oxygen within cerebral spinal fluid (CSF), pH of blood or CSF, glucose level in blood or CSF, protein marker of pain, such as glutamate or substance P, within CSF or subcutaneous extracellular fluid, non-facial muscular activity or tone, arterial blood flow, and galvanic skin response. Preferably, the non-PSG parameter set includes a plurality of these physiological parameters. However, the non-PSG physiological parameter set does not include physiological parameters typically required for PSG, such as brain electrical activity (electroencephalogram), eye movement (electro-oculogram), and chin or jaw muscular activity or tone (electromyogram). Consequently, as used herein, the terms "non-polysomnographic physiological parameter set" and "non-PSG physiological parameter set" refer to a set of one or more physiological parameters that does not include the physiological parameters typically required for PSG, such as brain electrical activity (electroencephalogram), eye movement (electro-oculogram), and chin or jaw muscular activity or tone (electromyogram).

Values of the non-PSG physiological parameter set are correlated to PSG-determined sleep states for a plurality of experimental subjects. The correlated values of the non-PSG parameter set and sleep states for the plurality of experimental subjects may be analyzed, and a relationship that allows determination of sleep states for any given patient based on values of the non-PSG physiological parameter set for the patient may be developed based on the analysis. Medical devices, such as implantable medical devices (IMDs) that would generally be unable to monitor such physiological parameters typically required for PSG, may be able to monitor the non-PSG physiological parameter set. Such a medical device may apply the relationship to values of the non-PSG physiological parameter set of a patient to identify sleep states of the patient. The medical device may control delivery of therapy to the patient, or monitor the quality of the patient's sleep based on the identified sleep states.

For each of the plurality of experimental subjects, values of a PSG physiological parameter set and a non-PSG physiological parameter set may be collected at the same time over the course of one or more sleep periods. The values may be collected, for example, in a sleep laboratory, and the values of the PSG physiological parameter set may be collected using equipment commonly available at such laboratories. The PSG physiological parameter set may include brain electrical activity, eye movement, and chin or jaw muscular activity or tone. Consequently, values of the PSG physiological parameter set for a subject may be collected via an array of electro-encephalogram (EEG) electrodes placed on the scalp of the subject, a plurality of electro-oculogram (EOG) electrodes placed proximate to the eyes of the subject, and one or more electromyogram (EMG) electrodes placed on the chin or jaw of the subject. The PSG physiological parameter set may also include other physiological parameters, such as heart rate, respiration rate, and blood oxygen saturation level, and the subject may be coupled to or otherwise wear sensors known for sensing such physiological parameters.

One or more external data recorders and/or a computer may receive the signals from the electrodes and other sensors that sense the PSG physiological parameter set of the subject. In either case, a computer receives values of the PSG physiological parameter set. The computer may display the values of the PSG physiological parameter set to a physician or technician for "scoring," e.g., identification of the times that the subject was within various sleep states using techniques known in the art. In other embodiments, the computer may automatically identify the times that the subject was within various sleep states based on the values of the PSG physiological parameter set collected for the subject.

During the one or more nights of data collection, the subject is also coupled to or otherwise wears a plurality of sensors that sense the non-PSG physiological parameter set. An external data recorder may receive the signals from such sensors and, in some embodiments, may house one or more of the sensors. For example, the external data recorder may be configured to be worn by the subject, and may house one or more sensors for detecting subject activity and/or posture, such as a three-axis accelerometer that generates a signal as a function of subject activity and posture.

The external data recorder stores the signals received from the sensors for subject, and provides the signals to a computer for correlation with the sleep states identified for the subject. The computer may be the same computer used to identify sleep states based on the PSG physiological parameter set, or a different computer. The external data recorder may transmit the stored signals to the computer via a wireless connection or data cable. In other embodiments, the external data recorder may provide the stored signals to the computer by storing the signals on a removable medium, such as a flash memory, that is receivable by the computer. In addition to correlating values of the non-PSG physiological parameter set with sleep states for a particular subject, the computer, or another computer, may be used to analyze the correlated values and sleep states for a plurality of subjects, and determine a relationship between values of the non-PSG physiological parameter set and sleep states, as described above.

Additionally, as described above, a relationship between non-PSG physiological parameter values and sleep states may be determined based on PSG and non-PSG data collected from a plurality of subjects. Such a relationship may be used in medical devices of any number of patients—who may be different from the experimental subjects—to identify sleep states of the patients. In other words, a "global" relationship between values of a non-PSG physiological parameter set and sleep states may be determined based on the data collected from a plurality of experimental subjects, and used in any medical device that includes or is coupled to sensors that sense physiological parameters of the non-PSG physiological parameter set to identify sleep states of any patient.

In other embodiments, values of the non-PSG physiological parameter set may be correlated to PSG-determined sleep states for a single patient, the correlated values of the non-PSG parameter set and sleep states for the single patient may be analyzed, and a relationship that allows determination of sleep states for the patient based on values of the non-PSG physiological parameter set for the patient may be developed based on the analysis. Such a relationship may be used by a medical device of that particular patient to determine sleep states. In such embodiments, the medical device includes or is coupled to non-PSG sensors, and may be used record values for the non-PSG physiological parameters, instead of a separate data recorder, during the period of data collection prior to determination of the relationship.

In one embodiment, the invention is directed to a method comprising identifying sleep states of a subject during a period of time based on polysomnography, recording values of a non-polysomnographic physiological parameter set of the subject during the period of time, and correlating the recorded values of the non-polysomnographic physiological parameter set to the identified sleep states.

In another embodiment, the invention is directed to a system including a first plurality of sensors that sense a polysomnographic physiological parameter set of a subject, a second plurality of sensors that sense a non-polysomnographic physiological parameter set of the subject, and a processor. The processor receives signals sensed by the first and second pluralities of sensors during a period of time, determines values of the polysomnographic physiological parameter set and the non-polysomnographic physiological parameter set based on the signals, and correlates the values of the non-polysomnographic physiological parameter set with sleep states identified based on values of the polysomnographic physiological parameter set.

In another embodiment, the invention is directed to a system comprising means for recording values of a non-polysomnographic physiological parameter set of the subject during a period of time, and means for correlating the recorded values of the non-polysomnographic physiological parameter set to the sleep states identified by polysomnography during the period of time.

In another embodiment, the invention is directed toward a computer-readable medium comprising instructions. The instructions cause a programmable processor to record values of a non-polysomnographic physiological parameter set of the subject during a period of time, and correlate the recorded values of the non-polysomnographic physiological parameter set to the sleep states identified by polysomnography during the period of time.

The invention may be capable of providing one or more advantages. For example, correlation of values of a non-PSG physiological parameter set to identified sleep states for each of a plurality of experimental subjects may facilitate determination of a relationship between values of the non-PSG physiological parameter set and sleep states. The determined relationship may allow patient medical devices that are not configured to sense PSG physiological parameters to identify sleep states of patients based on the non-PSG physiological parameter set. Such medical devices may, for example, control delivery of therapy to the patient, or monitor patient sleep quality based on the identified sleep states. By monitoring patient sleep quality, such medical devices may enable, for example, evaluation of the progression of an ailment or the effectiveness of a therapy delivered to treat the ailment.

Additionally, an external data recorder may be capable of receiving signals for a plurality of non-PSG physiological parameters. Analysis of the correlation between such parameters and identified sleep states may allow identification of a subset of such parameters that are more indicative of sleep state. This subset of non-PSG physiological parameters may form the non-PSG physiological parameter set used to identify patient sleep states in a patient medical device.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
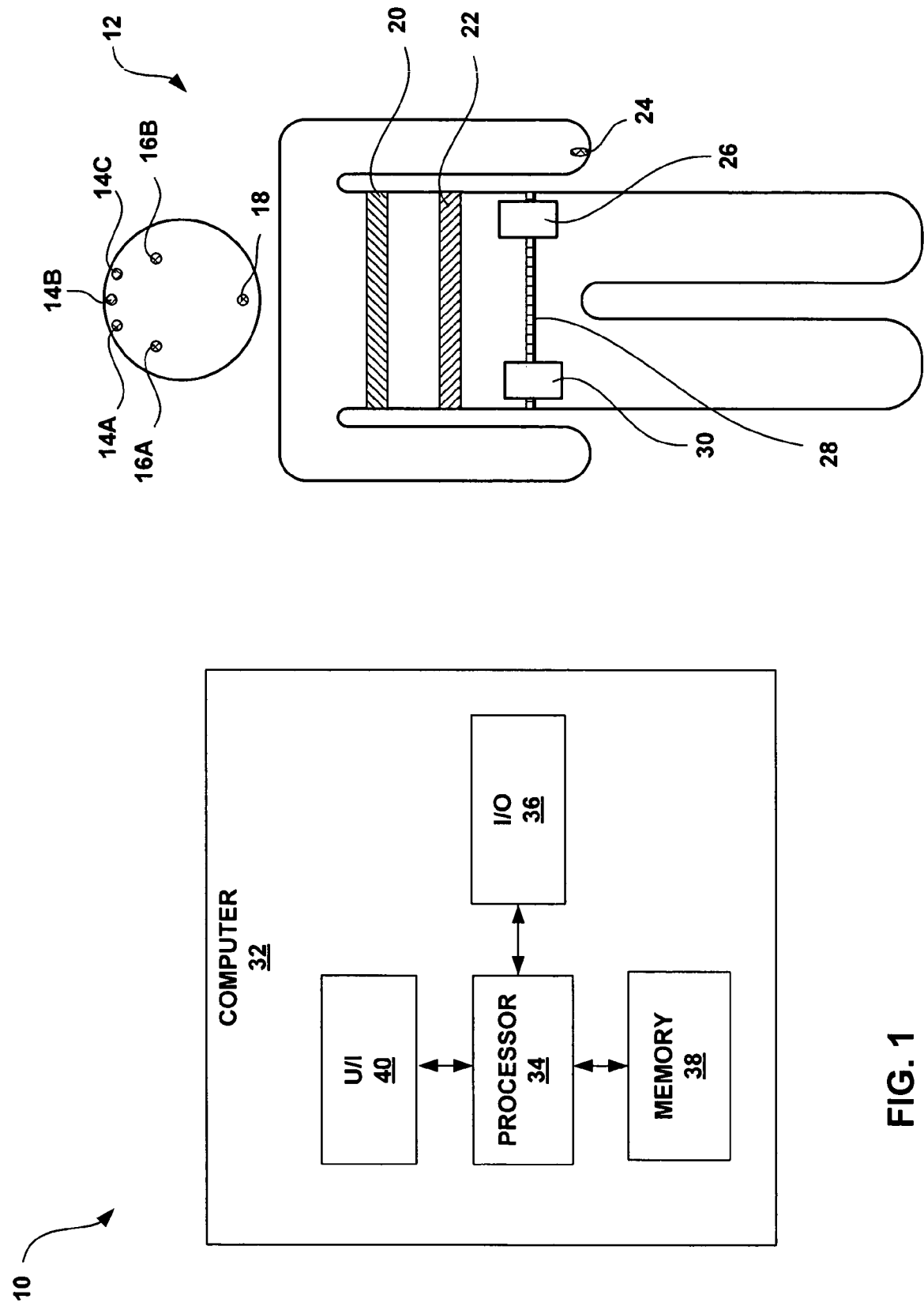
FIG. 1 is a conceptual diagram illustrating an example system for collection and analysis of values of a polysomnographic (PSG) physiological parameter set and a non-PSG physiological parameter set.

FIG. 1 is a conceptual diagram illustrating an example system 10 for collection and analysis of values of a polysomnographic (PSG) physiological parameter set and a non-PSG physiological parameter set for an experimental subject 12. The values of the PSG and non-PSG physiological parameter sets are collected at the same time to facilitate correlation of the values of the non-PSG physiological parameter set with sleep states of subject 12 identified based on the PSG physiological parameter set. The collection of the values for subject 12 may occur at a sleep laboratory over the course of one or more sleep periods, e.g., one or more nights, and some or all of the components of system 10 may be located at the sleep laboratory. The analysis of the values may occur at the sleep laboratory, or at some other location.

The PSG physiological parameter set may include brain electrical activity, eye movement, and chin, jaw or neck muscular activity or tone. Consequently, values of the PSG physiological parameter set for subject 12 may be collected via an array of electroencephalogram (EEG) electrodes 14A-C (collectively "EEG electrodes 14") placed on the scalp of subject 12, a plurality of electro-oculogram (EOG) electrodes 16A and 16B (collectively "EOG electrodes 16") placed proximate to the eyes of subject 12, and one or more electromyogram (EMG) electrodes 18 placed on the chin or jaw of the subject. The number and positions of electrodes 14, 16 and 18 illustrated in FIG. 1 are merely exemplary. For example, although only three EEG electrodes 14 are illustrated in FIG. 1, an array of between 16 and 25 EEG electrodes 14 may be placed on the scalp of subject 12, as is known in the art. EEG electrodes 14 may be individually placed on subject 12, or integrated within a cap or hair net worn by subject 12.

The non-PSG physiological parameter set may include, for example, one or more of posture, activity level, heart rate, electrocardiogram (ECG) morphology, respiration rate, respiratory volume, blood pressure, blood oxygen saturation, core temperature, partial pressure of oxygen within blood, partial pressure of oxygen within cerebral spinal fluid (CSF), pH of blood or CSF, glucose level in blood or CSF, protein marker of pain, such as glutamate or substance P, within CSF or subcutaneous extracellular fluid, non-facial muscular activity or tone, arterial blood flow, and galvanic skin response. Preferably, the non-PSG parameter set includes a plurality of these physiological parameters. In some embodiments, the non-PSG physiological parameter set may include the variability of one or more of these parameters, such as heart rate and respiration rate. The non-PSG physiological parameter set does not include physiological parameters typically required for PSG, such as brain electrical activity (EEG), eye movement (EOG), and chin or jaw muscular activity or tone (EMG).

In the illustrated example, subject 12 wears an ECG belt 20. ECG belt 20 incorporates a plurality of electrodes for sensing the electrical activity of the heart of subject 12. The heart rate and, in some embodiments, ECG morphology of subject 12 may be monitored based on the signal provided by ECG belt 20. Examples of suitable belts 20 for sensing the heart rate of subject 12 are the "M" and "F" heart rate monitor models commercially available from Polar Electro. In some embodiments, instead of belt 20, subject 12 may wear a plurality of ECG electrodes attached, e.g., via adhesive patches, at various locations on the chest of the subject, as is known in the art. An ECG signal derived from the signals sensed by such an array of electrodes may enable both heart rate and ECG morphology monitoring, as is known in the art.

As shown in FIG. 1, subject 12 may also wear a respiration belt 22 that outputs a signal that varies as a function of respiration of the subject. Respiration belt 22 may be a plethysmography belt, and the signal output by respiration belt 22 may vary as a function of the changes in the thoracic or abdominal circumference of subject 12 that accompany breathing by the subject. An example of a suitable belt 22 is the TSD201 Respiratory Effort Transducer commercially available from Biopac Systems, Inc. Alternatively, respiration belt 22 may incorporate or be replaced by a plurality of electrodes that direct an electrical signal through the thorax of the subject, and circuitry to sense the impedance of the thorax, which varies as a function of respiration of the subject, based on the signal. In some embodiments, ECG and respiration belts 20 and 22 may be a common belt worn by subject 12, and the relative locations of belts 20 and 22 depicted in FIG. 1 are merely exemplary.

In the example illustrated by FIG. 1, subject 12 also wears a transducer 24 that outputs a signal as a function of the oxygen saturation of the blood of subject 12. Transducer 24 may be an infrared transducer. Transducer 24 may be located on one of the fingers or earlobes of subject 12.

Although not shown in FIG. 1, subject 12 may wear or otherwise be connected to sensors for sensing other non-PSG physiological parameters, such as posture, activity level, blood pressure, core temperature, partial pressure of oxygen within blood, partial pressure of oxygen within CSF, pH of blood or CSF, glucose level in blood or CSF, protein marker of pain, such as glutamate or substance P, within CSF or subcutaneous extracellular fluid, non-facial muscular activity or tone, arterial blood flow, and galvanic skin response. In some cases, such sensors may be percutaneously or fully implanted within subject 12. Types of sensors useful for sensing these additional physiological parameters will be discussed in greater detail below. In general, because they are being applied to experimental subjects, less invasive types of sensors may be selected where possible.

System 10 may also include a non-PSG external data recorder 26 that receives and stores signals from belts 20 and 22, transducer 24, and any other non-PSG sensors worn or otherwise connected to subject 12. The belts, transducer and any other sensors may be connected to external data recorder 26 via wires, or wireless connections. The connections between the belts, transducer and external data recorder are not shown in FIG. 1 for ease of illustration.

As will be described in greater detail below, the data collected by external data recorder 26 may be used to experimentally determine a relationship between non-PSG physiological parameter values and sleep states. Medical devices, such as implantable medical devices (IMDs) may use the determined relationship to identify sleep states of patients based on non-PSG physiological parameter set values collected via sensors. Consequently, it may be desired that the external data recorder collects non-PSG physiological parameter values in a way to approximate collection of such parameter values by a medical device. Accordingly, external data recorder 26, which may incorporate sensors, and/or sensors coupled to the external data recorder, may be positioned on subject 12 at locations that are proximate to the locations where such sensors would be positioned within or on a patient who has such a medical device. For example, external data recorder 26 or sensors coupled to the data recorder may be positioned on subject 12 proximate to an implant location for an IMD, e.g., proximate to the lower back or abdomen of the subject.

As shown in FIG. 1, external data recorder 26 may be configured to be worn by subject 12. In the illustrated example, external data recorder 26 is carried by or attached to a belt 28 worn by subject 12 during the course of one or more nights of data recording. Belt 28 may be worn about the waist of subject 12, as illustrated in FIG. 1, or around an arm or leg of the subject. External data recorder 26 may alternatively be, for example, attached to a harness worn by subject 12, or an item of subject's clothing. In some embodiments, external data recorder 26 or sensors coupled thereto are held in position by, or incorporated into, an undergarment of subject 12. For example, external data recorder 26 or sensors may be held in position by, or incorporated into, compression shorts or bands that maintain the data recorder or sensors substantially proximate to an IMD implant location.

In some embodiments, as indicated above, external data recorder 26 may house one or more sensors that sense non-PSG physiological parameters. For example, external data recorder 26 may house one or more sensors for detecting activity and/or posture of subject 12. In exemplary embodiments, external data recorder 26 houses a three-axis accelerometer that generates a signal as a function of activity and posture of the subject.

As shown in FIG. 1, system 10 may additionally include a PSG external data recorder 30 that receives and stores signals from electrodes 14, 16 and 18. The electrodes may be connected to PSG external data recorder 30 via wires, or wireless connections. The connections between the electrodes and PSG external data recorder are not shown in FIG. 1 for ease of illustration. Like non-PSG external data recorder 26, PSG external data recorder 28 may be configured to be worn by subject 12, e.g., on or attached to a belt, harness, or item of clothing of the subject. In the illustrated example, external data recorders 26 and 30 are carried by or attached to a common belt 28.

In some embodiments, the PSG physiological parameter set may include other physiological parameters in addition to brain electrical activity, eye movement and chin or jaw muscle tension or activity. For example, in some embodiments, the PSG physiological parameter set may include heart rate, respiration rate or volume, blood oxygen saturation, or other physiological parameters that are also part of the non-PSG physiological parameter set. In such embodiments, PSG external data recorder 30 may be connected to separate, e.g., redundant, sensors, or may be coupled to the same sensors, such as belts 20 and 22 and transducer 24, as non-PSG external data recorder 26. Alternatively, in some embodiments in which there is overlap between the PSG and non-PSG physiological parameter sets, only one of external data recorders 26 and 30 may receive and store a signal from a sensor that senses a common physiological parameter. In such embodiments, a computer that receives the stored signal from the one of the external data recorders 26 and 30 may "assign" the signal, or values derived therefrom, to both the PSG and non-PSG physiological parameter sets for presentation to a user and/or analysis, which will be described in greater detail below.

In the example illustrated by FIG. 1, system 10 includes a computer 32 that receives the sensor signals stored by external data recorders 26 and 30, e.g., over the course of a night, from the external data recorders. More particularly, a processor 34 of computer 32 receives the signals via input/output (I/O) circuitry 36 of the computer. I/O circuitry 36 may include, for example, circuitry for interfacing with a data cable, such as a Universal Serial Bus (USB) cable, coupled to one of data recorders 26 and 30.

I/O circuitry 36 may additionally or alternatively include a wireless transceiver for wireless communication with one or both of external data recorders 26 and 30. The wireless transceiver may be configured for communication according to any of a variety of local wireless communication techniques, such as RF communication according to the 802.11 or Bluetooth specification sets, infrared communication according to the IRDA specification set, or other standard or proprietary telemetry protocols. In other embodiments, external data recorders 26 and 30 may store the signals within a removable medium, such as a flash memory. In such embodiments, computer 32 may be configured to receive the removable medium, and I/O circuitry 36 may include circuitry to retrieve the signals from the medium. Further, in still other embodiments, I/O circuitry 36 may include a network interface that allows processor 34 to receive the signals via a computer network, such as a local or wide area network, or the Internet. In other words, computer 32 may be located remotely from recorders 26 and 30.

In some embodiments, rather than storing signals received from sensors 14-24, data recorders 26 and 30 may transmit the signals to I/O circuitry 36 in real time via, for example, a data cable or wireless connection. In still other embodiments, system 10 may not include one or both of external data recorders 26 and 30. In such embodiments, I/O circuitry 36 may receive signals directly from sensors in real time via wired or wireless connections.

Processor 34 may store the received signals, or values derived therefrom, such as minimum, maximum, slope, mean or median values over periods of time, in a memory 38. In some embodiments, processor 34 may derive such values based on the signals received from external data recorders 26 and 30, or directly from the sensors. In other embodiments, external data recorders 26 and 30 may derive such values from the signals received from the sensors, and provide the values to processor 34. In embodiments in which there is overlap between the PSG and non-PSG physiological parameter sets, processor may "assign" a signal, or values derived therefrom, to both the PSG and non-PSG physiological parameter sets within memory 38.

Processor 34 may present values for the PSG physiological parameter set to a user, such as a clinician or technician, via a user interface 40. User interface 40 may include a monitor or other display device, a keyboard, and a pointing device, such as a mouse, trackball or stylus. Processor 34 may present values for the PSG physiological parameter set as one or more "traces" over time on a display of user interface 38. The user may "scroll" through, or otherwise manipulate, the physiological parameter traces via a keyboard or pointing device of user interface 40. User interface 40 may additionally or alternatively include a printer, and processor 34 may present values for the PSG physiological parameter set, e.g., as one or more "traces" over time, to a user via the printer.

The user may "score" the values for the PSG physiological parameter set using techniques known in the art to identify times at which subject 12 was within various sleep states. For example, the user may identify the times at which subject 12 was asleep, within the rapid eye movement (REM) sleep state, and within each of the nonrapid eye movement (NREM) sleep states (S1, S2, S3, S4). The user may "mark" the time at which the subject was within the various sleep states on the PSG physiological parameter set trace using the keyboard or pointing device. Alternatively, processor 34 may analyze the values for the PSG physiological parameter set to automatically identify the times at which subject 12 was within the various sleep states. In either case, processor 34 may store indications of the times at which subject 12 was within the various sleep states within memory 38.

Processor 34 correlates, e.g., according to time, values of the non-PSG physiological parameter set for subject 12 with the identified sleep states of subject 12 within memory 38. Processor 34 may receive values of the PSG and non-PSG physiological parameter sets for a plurality of experimental subjects 12, and may correlate PSG-determined sleep states with the values of the non-PSG physiological parameter set within memory 38 for each of the plurality of subjects. A plurality of systems 10 located at a plurality of facilities, e.g., sleep laboratories, may receive and analyze values of the PSG and non-PSG physiological parameter sets in this manner.

Computer 32 may be used to analyze the correlated values and sleep states for the plurality of subjects, and determine a relationship between values of the non-PSG physiological parameter set and sleep states. In some embodiments, processor 34 may analyze the correlations and determine the relationship. The relationship may allow determination of sleep states for any given patient based on values of the non-PSG physiological parameter set for the patient. Medical devices, such as implantable medical devices (IMDs) that would generally be unable to monitor such physiological parameters typically required for PSG, may be able to monitor the non-PSG physiological parameter set. Such a medical device may apply the relationship to values of the non-PSG physiological parameter set of a patient to identify sleep states of the patient. The medical device may control delivery of therapy to the patient, or monitor the quality of the patient's sleep based on the identified sleep states.

Computer 32 may include, for example, a personal computer, workstation, or network server. Processor 34 may include any one or more of a microprocessor, a controller, digital signal processor (DSP), application specific integrated circuit (ASIC), field-programmable gate array (FPGA), discrete logic circuitry, or the like. Memory 38 may include any of a variety of fixed or removable magnetic, electrical, or optical media, such as random access memory (RAM), read-only memory (ROM), CD-ROM, electronically-erasable programmable ROM (EEPROM), non-volatile RAM (NVRAM), flash memory, or the like. Memory 38 may store program instructions that, when executed by processor 34, cause processor 34 to perform the functions ascribed to it and computer 32 herein. In other words, the invention contemplates computer-readable media comprising instructions that cause a processor to perform the functions ascribed to processor 34 and computer 32 herein.

Figure 2:
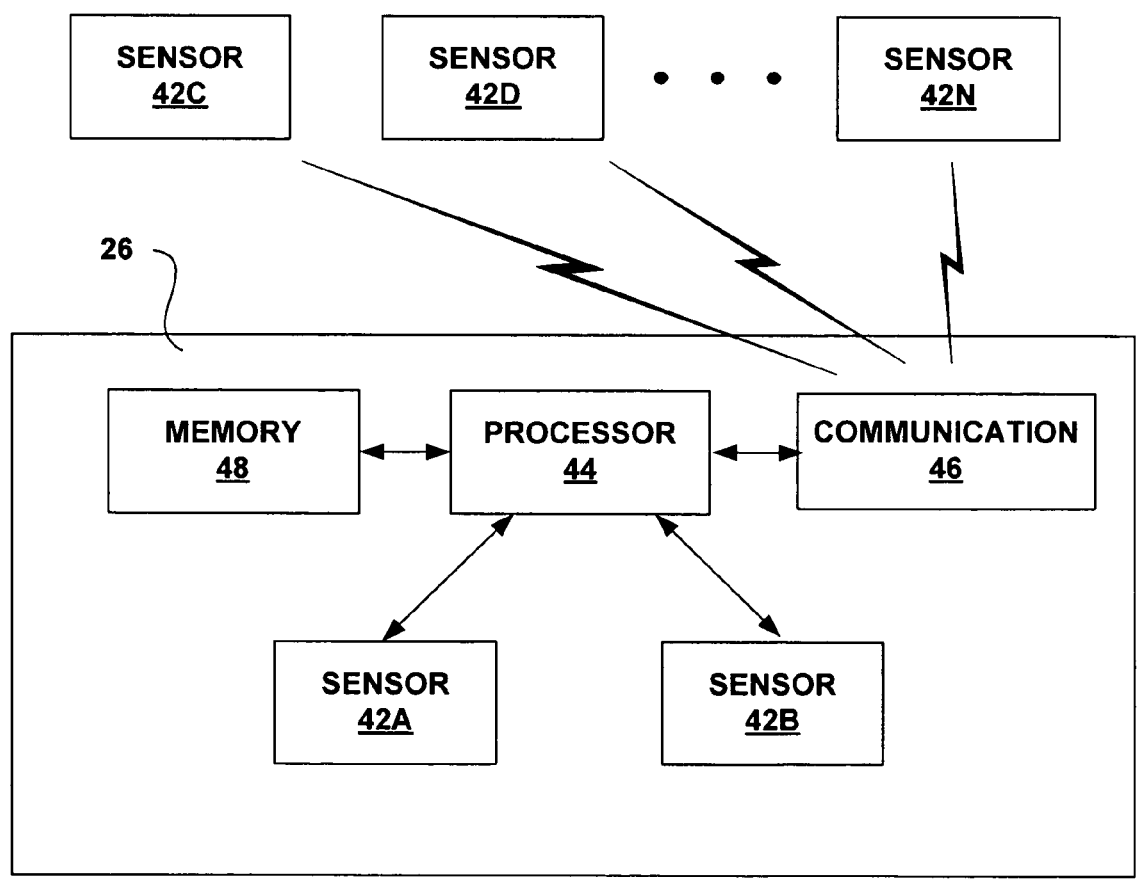
FIG. 2 is a block diagram illustrating an example configuration of a non-PSG recording portion of the system of FIG. 1 in greater detail.

FIG. 2 is a block diagram illustrating an example configuration of a non-PSG recording portion of system 10. In the illustrated example, the non-PSG portion of system 10 includes non-PSG external data recorder 26, and a plurality of sensors 42A-N (collectively "sensors 42") that sense physiological parameters within the non-PSG physiological parameter set. As shown in FIG. 2, external data recorder 26 may house some sensors 42, while other sensors 42 are connected to the external data recorder.

In the illustrated example, sensors 42 that are external to non-PSG data recorder 26 are wirelessly connected, e.g., via a radio-frequency (RF) medium, to the data recorder. Such sensors 42 may communicate with non-PSG data recorder 26 according to any of a variety of local wireless communication protocols, such as the Bluetooth protocol, or one of the 802.11 protocols. Sensors 42 that are external to non-PSG data recorder 26 may additionally or alternatively be connected to the data recorder via wires, cables, or the like.

In addition to sensors 42, non-PSG external data recorder 26 may include a processor 44, communication circuitry 46 and memory 48, as shown in FIG. 2. Processor 44 receives signals from sensors 42, each of the signals varying as a function of at least one of the physiological parameters of the non-PSG parameter set. Processor 44 stores the signals, or values derived from the signals such as minimum, maximum, slope, mean or median values, within memory 48.

In the illustrated embodiment, processor 44 wirelessly receives signals from sensors 42 external to data recorder 26 via communication circuitry 46. In some embodiments, communication circuitry 46 includes a wireless transceiver compliant with any of a variety of wireless communication protocols, such as the Bluetooth or 802.11 protocols. In other embodiments, processor 46 receives the signals via wires, cables, leads, or the like. In such embodiments, external data recorder 26 may include circuitry (not shown) that conditions the signals generated by sensors 42 such that they may be analyzed by processor 44. For example, external data recorder 26 may include one or more analog to digital converters to convert analog signals generated by sensors 42 into digital signals usable by processor 44, as well as suitable filter and amplifier circuitry.

Processor 44 may also provide the signals or values stored in memory 48 to a computer 32 via communication circuitry 46. Communication circuitry 46 may include a wireless transceiver, as described above, for wireless transmission of the values or data to the computer. In other embodiments, processor 44 provides the signals or values to computer 32 via a wired connection, such as a USB cable. In still other embodiments, memory 48 is a removable medium, such as a flash memory card, that is receivable and readable by computer 32 or a peripheral device coupled to the computer. In such embodiments, the signals or values are provided to computer 32 through transfer of the medium to the computer.

Processor 44 may include any one or more of a microprocessor, a controller, a DSP, an ASIC, an FPGA, discrete logic circuitry, or the like. Memory 48 may include any one or more volatile or non-volatile, removable or fixed, magnetic, optical, or electrical media, such as a RAM, ROM, CD-ROM, NVRAM, EEPROM, flash memory, or the like. In some embodiments, memory 48 stores program instructions that, when executed by processor 46, cause external data recorder 26 and processor 44 to perform the functions attributed to them herein.

As indicated above, the non-PSG physiological parameter set may include one or more of posture, activity level, heart rate, ECG morphology, respiration rate, respiratory volume, blood pressure, blood oxygen saturation, core temperature, partial pressure of oxygen within blood, partial pressure of oxygen within cerebral spinal fluid (CSF), pH of blood or CSF, glucose level in blood or CSF, protein marker of pain, such as glutamate or substance P, within CSF or subcutaneous extracellular fluid, non-facial muscular activity or tone, arterial blood flow, and galvanic skin response. In some embodiments, the non-PSG physiological parameter set may include the variability of one or more of these parameters, such as heart rate or respiration rate.

Sensors 42 may include, for example, one or more accelerometers, gyros, mercury switches, or bonded piezoelectric crystals that output a signal as a function of subject activity, e.g., body motion, footfalls or other impact events, and the like. Sensors 40 may additionally or alternatively include a plurality of accelerometers, gyros, or magnetometers oriented orthogonally that output signals which indicate the posture of subject 12. In addition to being oriented orthogonally with respect to each other, each of sensors 42 used to detect the posture of subject 12 may be generally aligned with an axis of the body of the subject. In exemplary embodiments, sensors 42 include three orthogonally aligned posture sensors.

When sensors 42 include accelerometers, for example, that are aligned in this manner, the magnitude and polarity of zero frequency components of the signals output by the accelerometers may indicate the orientation of subject 12 relative to the Earth's gravity, e.g., the posture of subject 12. The magnitude and frequency of non-zero frequency components of the signals, e.g., 0.1 Hz to 10 Hz, indicate the activity level of the subject. External data recorder 26 may include analog filtering circuitry, or one or both of processor 44 or processor 34 of computer 32 may apply digital filters to pass the respective bands of such sensor signals useful for posture and activity sensing. Further information regarding use of orthogonally aligned accelerometers to determine posture may be found in commonly assigned U.S. Pat. No. 5,593,431, which issued to Todd J. Sheldon.

As indicated above, such activity and posture detecting sensors 42 may be located within a housing of external data recorder 26. Additionally or alternatively, activity and posture detecting sensors may be connected to the external data recorder by a wired or wireless connection. For example, activity or posture detecting sensors 42 may be carried by a strap or the like worn by subject 12 on an arm or leg.

As another example, sensors 42 may include electrodes that generate an electrogram signal as a function of electrical activity of the heart of patient 12. Such electrodes may be included within an ECG belt 20, as described above. The signals output by such electrodes may indicate the heart rate of subject 12. The signals output by such electrodes and may also allow measurement of ECG morphological features, such as QRS amplitude or width, QT interval length, T-wave width or amplitude, or evoked response latency or amplitude. In other embodiments, sensors 42 may include one or more acoustic sensors located, for example, on the chest of subject 12, which output a signal that varies as a function of heart rate. In still other embodiments, sensors 42 may include percutaneously implanted temperature, flow or pressure sensors located within the bloodstream or cerebrospinal fluid (CSF) of subject 12, or a sphygmomanometer cuff. The signals generated by such sensors may vary as a function of contraction of the heart of subject 12, and thereby indicate the heart rate of subject 12.

Sensors 42 may also include sensors that output a signal that varies as a function of respiration by subject 12. For example, sensors 42 may include a respiration belt 22, as described above. In other embodiments, sensors 42 may include an implanted or external strain gauge, bonded piezoelectric element, or pressure sensor that generates a signal that varies based on respiration. An electrogram generated by electrodes as discussed above may also be modulated by patient respiration, and may be used as an indirect representation of respiration rate. In some embodiments, sensors 42 may include two or more electrodes, e.g., located on the chest of subject, that generate a signal as a function of the thoracic impedance of subject 12, which varies as a function of respiration by the subject. The thoracic impedance signal may also vary as a function of the posture of subject 12, and may therefore by used to sense the subject's posture.

Sensors 42 may include electrodes that generate an electromyogram (EMG) signal as a function of muscle electrical activity, or a strain gauge or the like located near or within a muscle that outputs a signal as a function of the mechanical activity or tension of the muscle. Such sensors 42 may be located, for example, on or within the legs, arms, buttocks, abdomen, or back of subject 12. The signals generated by such sensors when implanted in these locations may also vary based on the posture of patient 12, e.g., may vary based on whether the patient is standing, sitting, or lying down.

Sensors 42 may also include percutaneously implanted pressure sensors that output a signal as a function of a blood pressure, e.g., an arterial pressure, of subject 12, or a sphigmomanometery cuff that outputs a signal as a function of blood pressure. Further, sensors 42 may include any of a variety of known temperature sensors that output a signal as a function of a core temperature of subject 12. Such temperatures sensors may be, for example, located rectally or nasopharyngeally within subject 12.

Sensors 42 may also include optical, e.g., infrared, pulse oximetry sensors, which may be located on a finger or earlobe of subject 12, as discussed above. Further, sensors 42 may include a percutaneously implanted Clark dissolved oxygen sensor that outputs a signal as a function of blood or CSF oxygen partial pressure. Additionally, sensors 42 may include antimony electrodes that output a signal as a function of the pH of blood or CSF, and any of a variety of known chemical sensors that output a signal as a function of the level of glucose, or protein markers of pain, such as glutamate or substance P.

In some embodiments, sensors 42 may include one or more intraluminal, extraluminal, or external flow sensors positioned to generate a signal as a function of arterial blood flow. A flow sensor may be, for example, an electromagnetic, thermal convection, ultrasonic-Doppler, or laser-Doppler flow sensor. Further, sensors 42 may include one or more electrodes positioned on the skin of subject 12 to generate a signal as a function of galvanic skin response.

Figure 3:
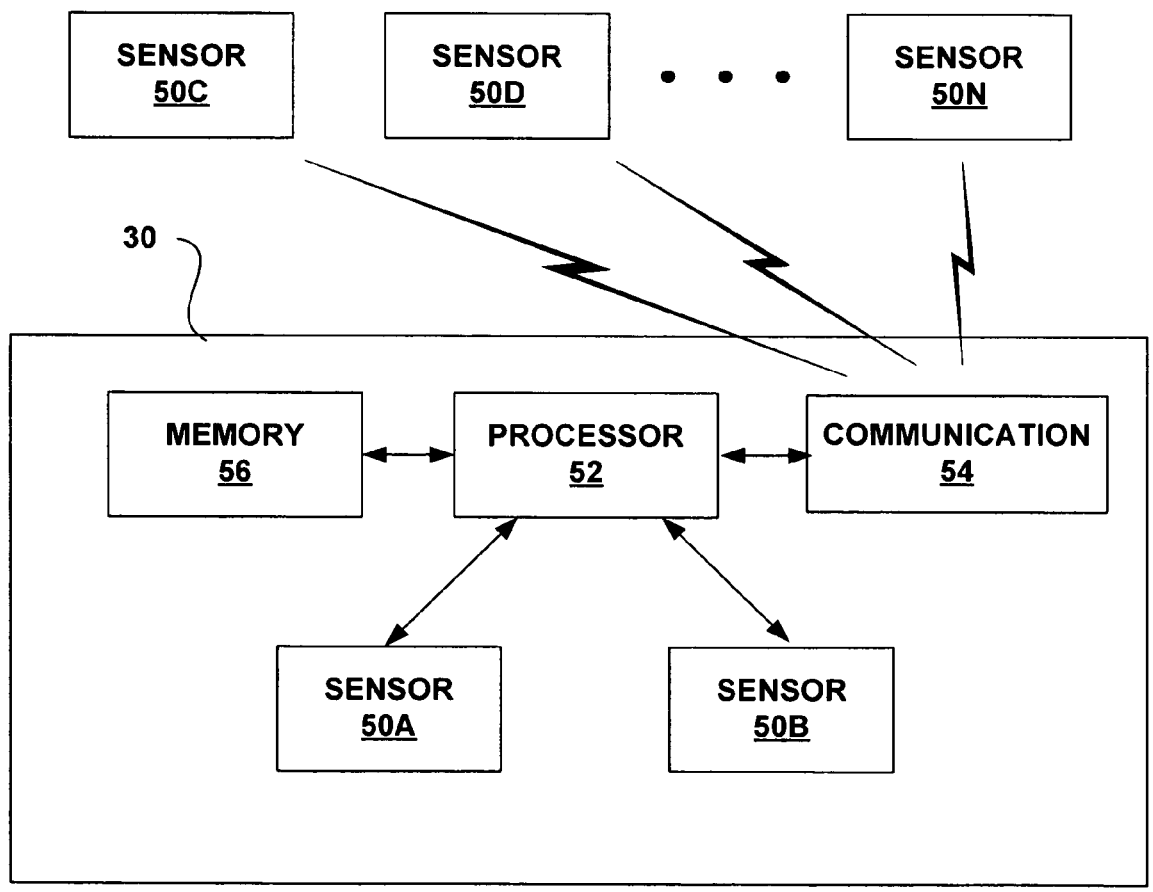
FIG. 3 is a block diagram illustrating an example configuration of a PSG recording portion of the system of FIG. 1 in greater detail.

FIG. 3 is a block diagram illustrating a PSG recording portion of system 10 in greater detail. In the illustrated example, the PSG portion of system 10 includes PSG external data recorder 30, and a plurality of sensors 50A-N (collectively "sensors 50") that sense physiological parameters within the PSG physiological parameter set. As shown in FIG. 3, external data recorder 30 may house some sensors 50, while other sensors 50 are connected to the external data recorder.

In the illustrated example, sensors 50 that are external to PSG data recorder 30 are wirelessly connected, e.g., via a radio-frequency (RF) medium, to the data recorder. Such sensors 50 may communicate with PSG data recorder 30 according to any of a variety of local wireless communication protocols, such as the Bluetooth protocol, or one of the 802.11 protocols. Sensors 50 that are external to PSG data recorder 30 may additionally or alternatively be connected to the data recorder via wires, cables, or the like.

In addition to sensors 50, PSG external data recorder 30 may include a processor 52, communication circuitry 54 and memory 56, which are substantially similar, and function substantially similarly to processor 44, communication circuitry 46 and memory 48 of non-PSG external data recorder 26 shown in FIG. 2.

As indicated above, the PSG physiological parameter set includes one or more of brain electrical activity, eye motion, and chin or jaw muscular activity or tone. Sensors 50 may include EEG electrodes 14, EOG electrodes 16 and EMG electrodes 18. Because the PSG physiological parameter set may also include one or more of the physiological parameters within the non-PSG physiological parameter set, sensors 50 may also include one or more of the types of sensors discussed above with reference to sensors 42 of FIG. 2.

Figure 4:
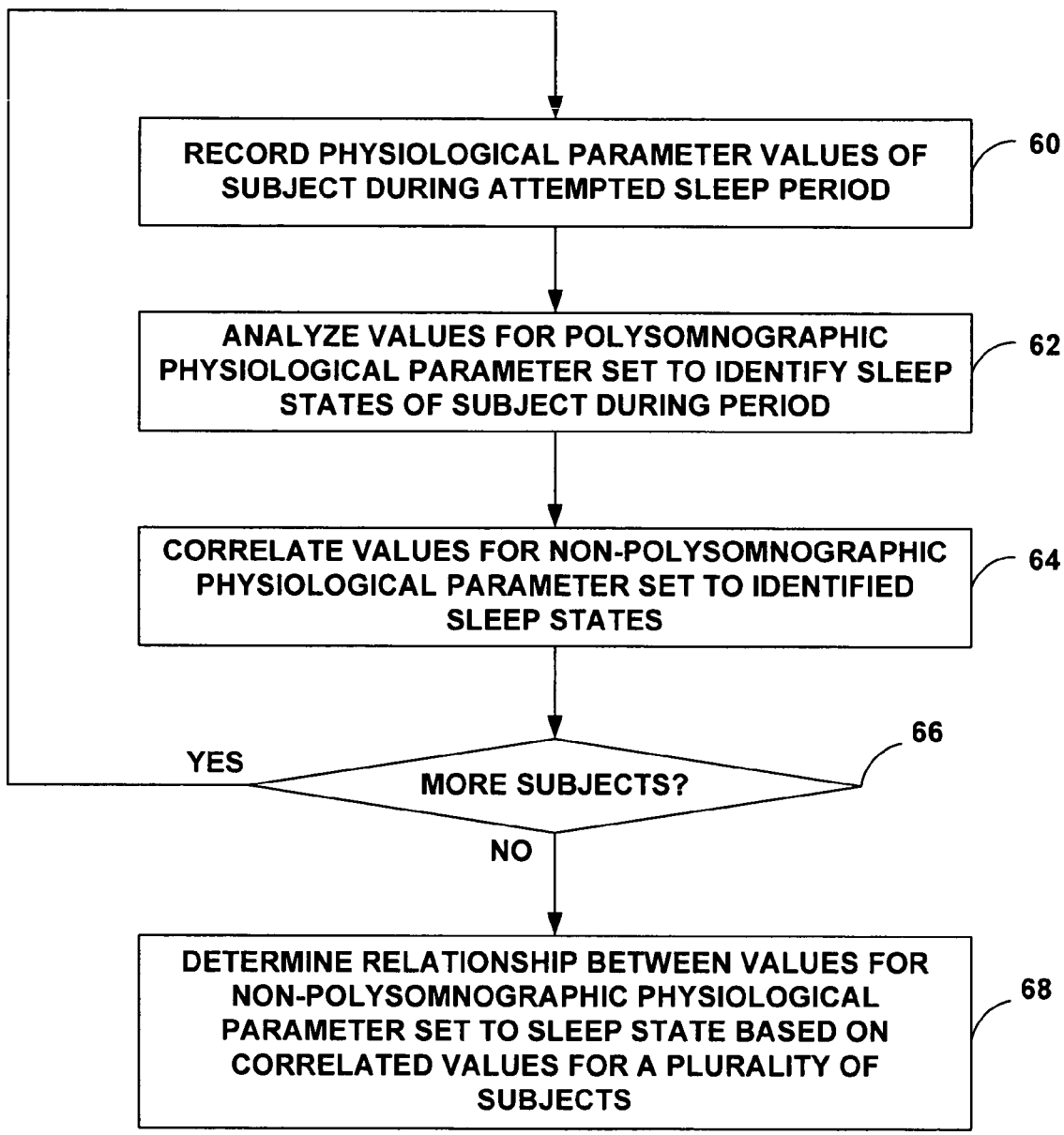
FIG. 4 is a flow diagram illustrating an example method for determining a relationship between values of a non-PSG physiological parameter set and sleep states.

FIG. 4 is a flow diagram illustrating an example method for determining a relationship between values of a non-PSG physiological parameter set and sleep states. According to the method, one or more external data recorders 26, 30, or a computer 32, record physiological parameter values of a subject 12 during an attempted sleep period, e.g., over the course of a night at a sleep laboratory (60). Computer 32 and/or a user of the computer analyzes values of a PSG physiological parameter set to identify the time at which the subject was within various sleep states during the period (62). Computer 32 correlates, e.g., according to time, values for a non-PSG physiological parameter set for subject 12 with the identified sleep states (64). Parameter values may be recorded, sleep states identified, and non-PSG parameter values correlated to the sleep states for each of a plurality of subjects 12 (66).

Computer 32 and/or a user of the computer may analyze the correlated values and sleep states for the plurality of subjects to determine a relationship between values for the non-PSG physiological parameter set and sleep states (68). Analyzing the correlated values may involve regression analysis, e.g., either linear or multiple regression. Analyzing the correlated values may additionally or alternatively involve deriving a polynomial equation with one or more terms that has an acceptable least-squares fit to the data. A subset of the experimental non-PSG physiological parameter set that is more predictive of sleep state may be identified based on the analysis, and used as the non-PSG physiological parameter set for the relationship. The relationship may take the form of any one or more thresholds, equations, look-up tables, neural networks, or the like.

Figure 5:
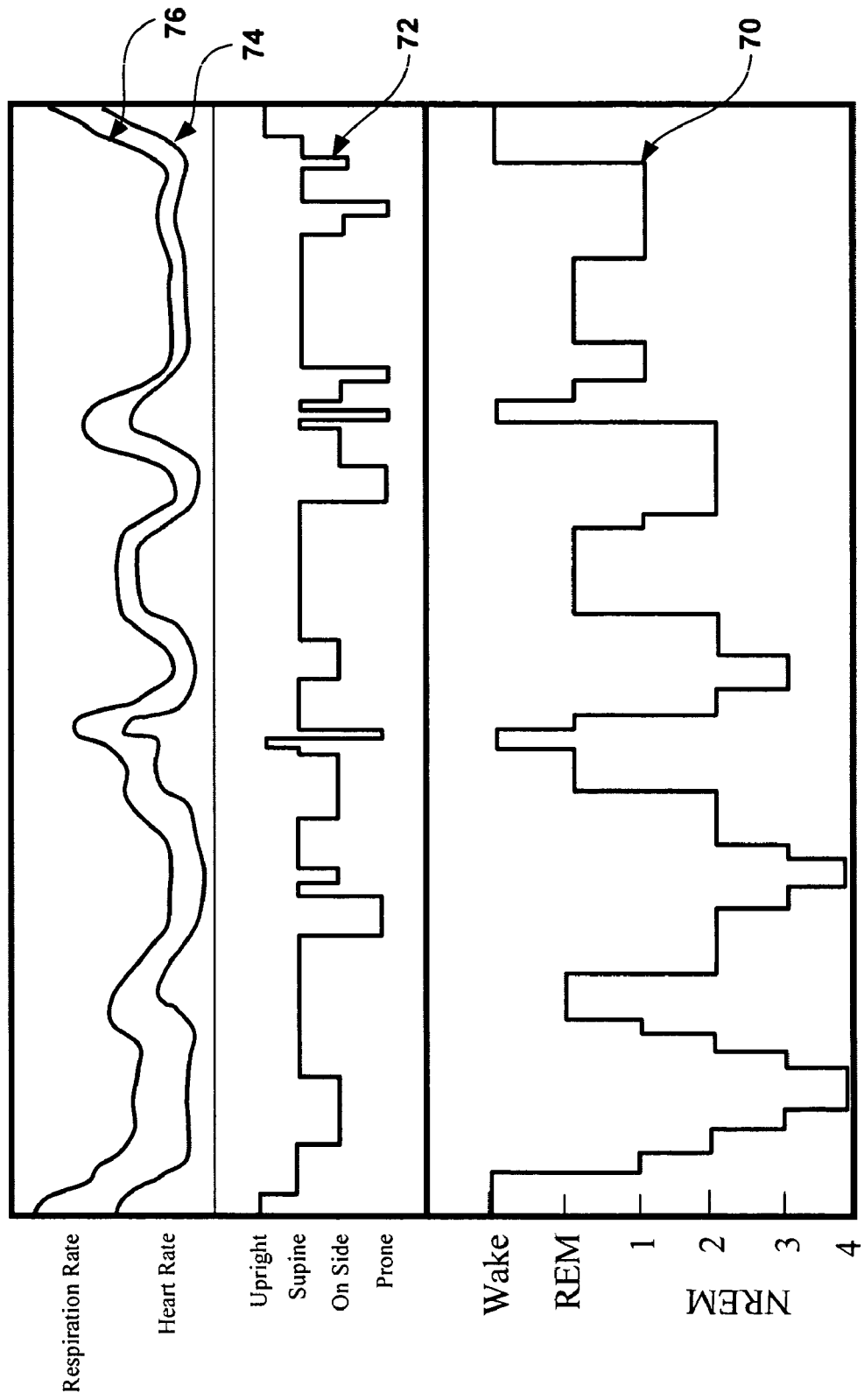
FIG. 5 is a timing diagram illustrating example PSG and non-PSG data.

FIG. 5 is a timing diagram illustrating example PSG and non-PSG data for a subject 12. In the illustrated example, the PSG and non-PSG data are correlated according to time. As discussed above, a user and/or processor 34 of computer 32 may analyze the correlated data to determine a relationship between values of non-PSG physiological parameters and sleep states.

FIG. 5 includes a graphical representation 70 of determined sleep states over time, i.e., a sleep profile or hypnogram. As discussed above, the sleep states may be determined by a user or a processor based on PSG physiological parameter values recorded for the subject. Further, as discussed above, fewer sleep states may be identified based on the PSG physiological parameter values. For example, in some embodiments, the sleep states identified may be awake and asleep, or awake, REM and NREM.

FIG. 5 also includes graphical representations of values of non-PSG physiological parameters over time. In particular, FIG. 5 includes graphical representation 72, 74, 76 of posture, heart rate and respiration rate, respectively, over time. However, the invention is not limited to embodiments that involve these example non-PSG physiological parameters. A number of examples of possible additional or alternative non-PSG physiological parameters are discussed above.

As discussed above, the heart rates and respiration rates indicated by representations 74 and 76 may be average rates. Further, in the illustrated example, a processor, such as processor 34 of computer 32, or processor 44 of external data recorder 26, has periodically characterized subject 12 as being in one of four possible postures (upright, supine, on side, or prone) based on signals generated by accelerometers or other sensors, as discussed above. Graphical representation 72 illustrates the result of such periodic characterization. However, the invention is not limited to embodiments in which these postures are identified, or in which postures are identified at all. For example, in some embodiments, processor 34 of computer 32 correlates the sensor signals themselves to sleep states without identifying postures.

Figure 6:
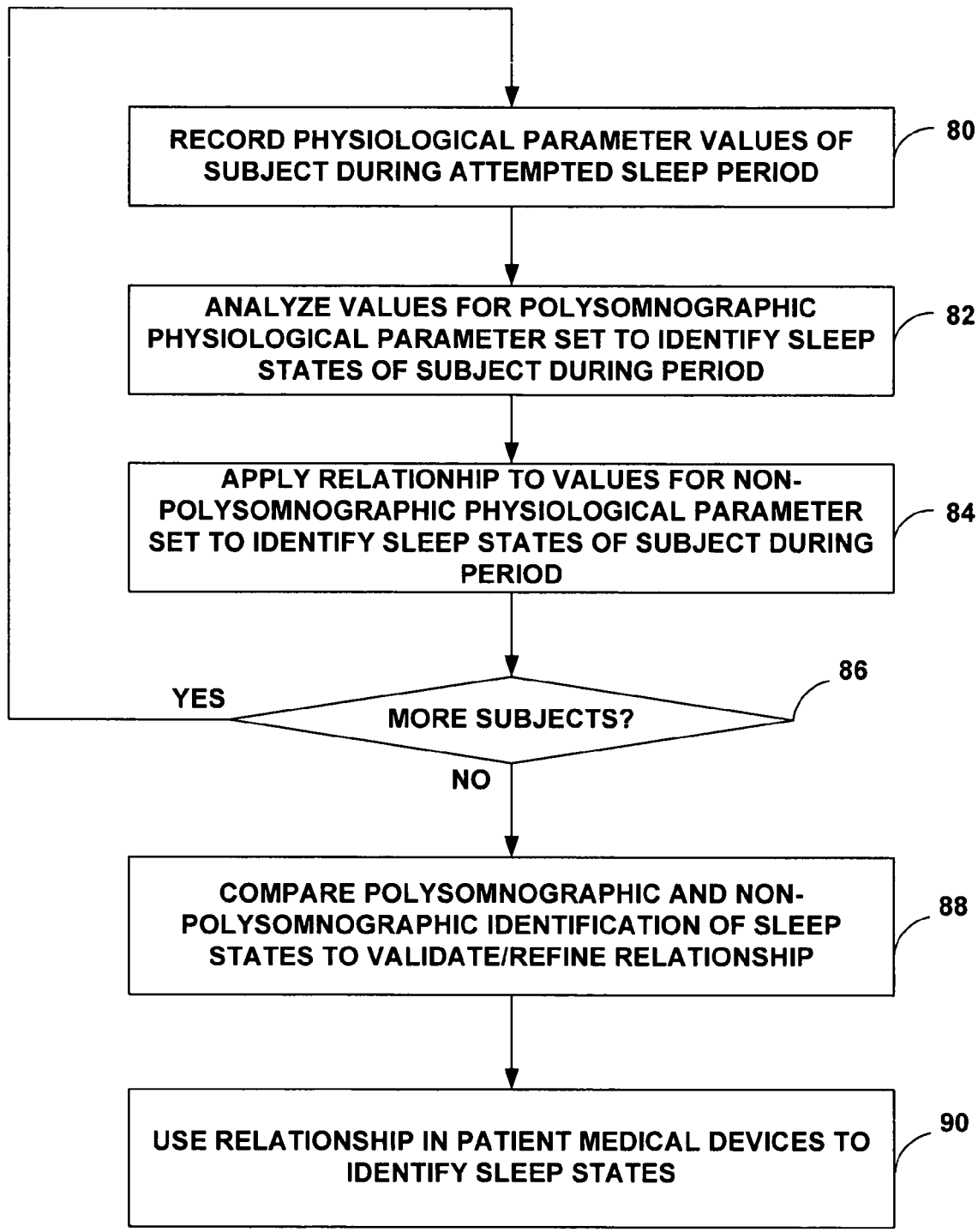
FIG. 6 is a flow diagram illustrating an example method for validating a determined relationship between values of a non-PSG physiological parameter set and sleep states.

FIG. 6 is a flow diagram illustrating an example method for validating a determined relationship between values of a non-PSG physiological parameter set and sleep states. According to the method, physiological parameter values are recorded, and values of the PSG physiological parameter set are analyzed to identify sleep states for a subject 12, as described above with reference to FIG. 4 (80, 82). The relationship is applied to a non-PSG physiological parameter set to identify sleep states for subject (84). The values are recorded and analyzed for identification of sleep states using both the PSG values and the relationship for each of a plurality of subjects 12 (86). The sleep states identified by the relationship may be compared to the PSG sleep states to validate and, if necessary, refine the relationship (88).

Once validated, the relationship may be used in patient medical devices to identify sleep states of patients (90). For example, the relationship may be used to identify sleep states for the purpose of evaluating sleep quality, which may in turn indicate the progression of an ailment or the effectiveness of a treatment for the ailment. As one example, sleep quality may provide an indication of the effectiveness of therapy parameter sets according to which a patient medical device delivers therapy to treat an ailment such as chronic pain. For a neurostimulator, as an example, a parameter set may include parameters that define a stimulation waveform, such as pulse amplitude, width and rate, as well as the electrodes from a set selected for delivery of the stimulation waveform. As another example, a parameter set for a drug delivery device may control the infusion rate and timing of the drug. Parameter sets may be evaluated as part of a trialing process, or over the course the medical device's use by, or implantation within, a patient.

The relationship may allow a variety of sleep quality metrics to be evaluated through identification of sleep states. For example, the relationship may identify when a patient is asleep. Sleep efficiency may be measured as the percentage of time while the patient is attempting to sleep that the patient is actually asleep. Sleep latency may be measured as the amount of time between a first time when the patient begins attempting to fall asleep and a second time when the patient falls asleep, and thereby indicates how long a patient requires to fall asleep.

Other sleep quality metrics that a medical device may determine using the relationship include total time sleeping per day, the amount or percentage of time sleeping during nighttime or daytime hours per day, and the number of apnea and/or arousal events per night. In some embodiments, a medical device may determine which sleep state the patient is in, e.g., rapid eye movement (REM), or one of the nonrapid eye movement (NREM) states (S1, S2, S3, S4) based on monitored physiological parameters, and the amount of time per day spent in these various sleep states may be determined by the medical device as a sleep quality metric. Because they provide the most "refreshing" type of sleep, the amount of time spent in one or both of the S3 and S4 sleep states, in particular, may be determined as a sleep quality metric.

Further, a medical device may control delivery of therapy to a patient based on identified sleep states, or sleep quality metrics determined based on identified sleep states. For example, a medical device may compare any of the sleep quality metrics identified above to a threshold value, and adjust one or more parameters of a delivered therapy based on the comparison. If, for example, the medical device is delivers electrical stimulation, e.g., is a neurostimulator, the medical device may adjust at least one of a pulse amplitude, pulse rate, pulse width and duty cycle of the stimulation based on the comparison. In this manner the medical device may adjust therapy to, for example, maintain adequate efficacy, which may be reflected in the quality of the patient's sleep.

Figure 7:
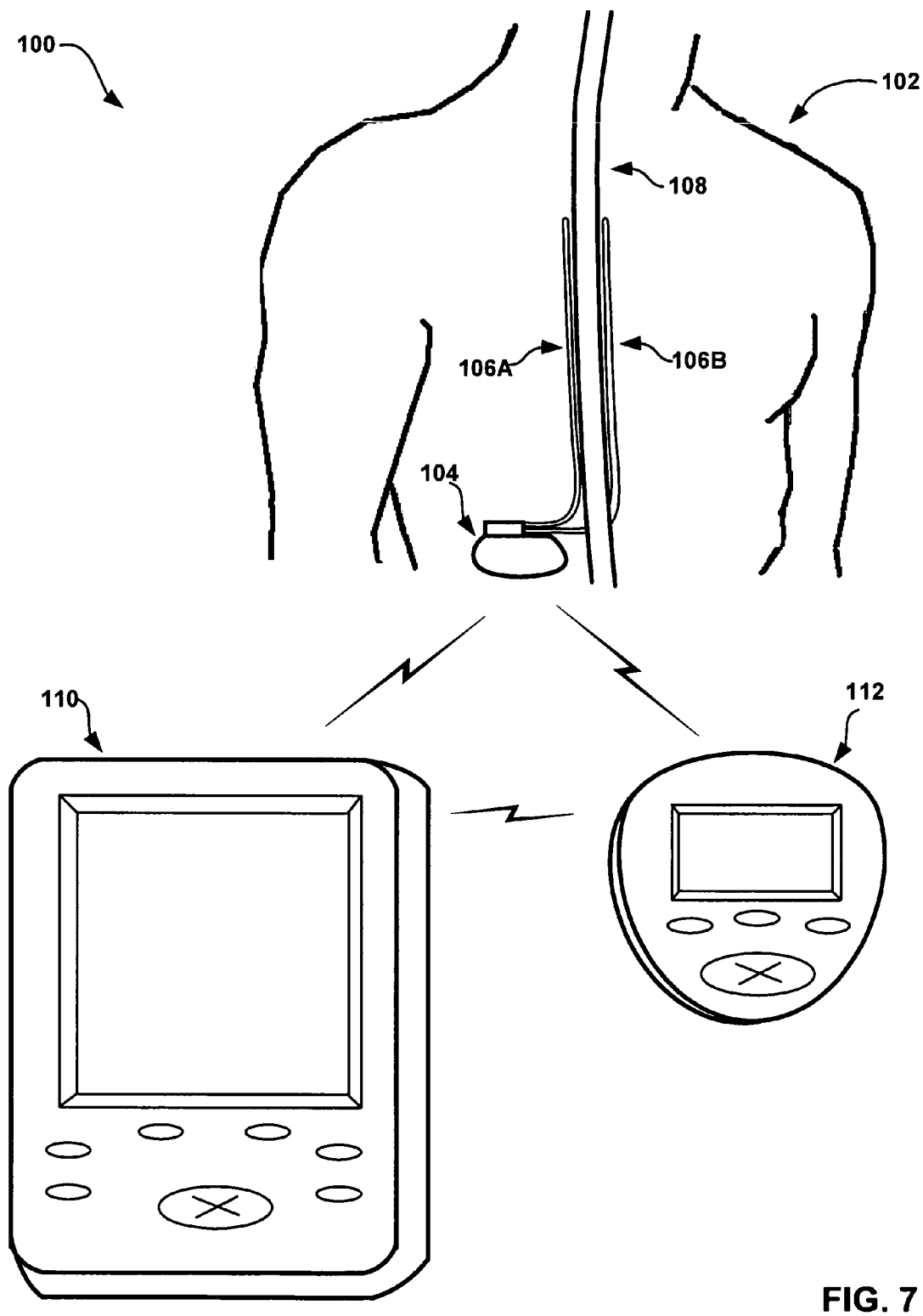
FIG. 7 is a conceptual diagram illustrating an example system including a medical device that applies the determined relationship to values of a non-PSG physiological parameter set to identify sleep states of a patient.

FIG. 7 is a conceptual diagram illustrating an example system 100 including a medical device that applies the determined relationship to values of a non-PSG physiological parameter set to identify sleep states of a patient 102. In the illustrated example, the medical device is an implantable medical device (IMD) 104 shown implanted within patient 102. More particular, in the illustrated example, IMD 104 takes the form of an implantable neurostimulator that delivers neurostimulation therapy in the form of electrical pulses to patient 102. IMD 104 delivers neurostimulation therapy to patient 102 via leads 106A and 106B (collectively "leads 106"). Leads 106 may, as shown in FIG. 1, be implanted proximate to the spinal cord 108 of patient 102, and IMD 104 may deliver spinal cord stimulation (SCS) therapy to patient 102 in order to, for example, reduce pain experienced by patient 12.

However, the invention is not limited to the configuration of leads 106 shown in FIG. 7, or to the delivery of SCS therapy. For example, one or more leads 106 may extend from IMD 104 to the brain (not shown) of patient 102, and IMD 104 may deliver deep brain stimulation (DBS) therapy to patient 102 to, for example, treat tremor, Parkinson's disease, multiple sclerosis, or epilepsy. As further examples, one or more leads 106 may be implanted proximate to the pelvic nerves (not shown) or stomach (not shown), and IMD 104 may deliver neurostimulation therapy to treat incontinence or gastroparesis.

Moreover, the invention is not limited to implementation via an implantable neurostimulator, or even implementation via an IMD. For example, in some embodiments of the invention, an implantable or external or cardiac rhythm management device, such as a pacemaker, or a drug delivery pump may control delivery of a therapy based on sleep quality information.

In the example of FIG. 7, IMD 104 delivers therapy according to a set of therapy parameters, i.e., a set of values for a number of parameters that define the therapy delivered according to that therapy parameter set. In embodiments where IMD 104 delivers neurostimulation therapy in the form of electrical pulses, the parameters for each parameter set may include voltage or current pulse amplitudes, pulse widths, pulse rates, and the like. Further, each of leads 106 includes electrodes (not shown in FIG. 1), and a therapy parameter set may include information identifying which electrodes have been selected for delivery of pulses, and the polarities of the selected electrodes. Therapy parameter sets used by IMD 104 may include a number of parameter sets programmed by a clinician (not shown), and parameter sets representing adjustments made by patient 102 to these preprogrammed sets.

In other non-neurostimulator embodiments of the invention, the IMD may still deliver therapy according to a therapy parameter set. For example, implantable pump IMD embodiments may deliver a therapeutic agent to a patient according to a therapy parameter set that includes, for example, a dosage, an infusion rate, and/or a duty cycle.

System 100 also includes a clinician programmer 110. A clinician (not shown) may use clinician programmer 110 to program therapy for patient 102, e.g., specify a number of therapy parameter sets and provide the parameter sets to IMD 104. The clinician may also use clinician programmer 110 to retrieve information collected by IMD 104. The clinician may use clinician programmer 110 to communicate with IMD 104 both during initial programming of IMD 104, and for collection of information and further programming during follow-up visits. In some embodiments, clinician programmer 110 may store or otherwise be able to access, e.g., via a network, a relationship between values of a non-PSG physiological parameter set and sleep states, determined as described above with reference to FIGS. 1-6. In such embodiments, clinician programmer 110 may be used to program IMD 104 with the relationship, e.g., transmit the relationship to IMD 104 for storage within a memory of the IMD.

System 100 also includes a patient programmer 112, which also may, as shown in FIG. 1, be a handheld computing device. Patient 102 may use patient programmer 112 to control the delivery of therapy by IMD 104. For example, using patient programmer 112, patient 102 may select a current therapy parameter set from among the therapy parameter sets preprogrammed by the clinician, or may adjust one or more parameters of a preprogrammed therapy parameter set to arrive at the current therapy parameter set.

However, clinician and patient programmers 110, 112 are not limited to the hand-held computer embodiments illustrated in FIG. 1. Programmers 110, 112 according to the invention may be any sort of computing device. For example, a programmer 110, 112 according to the invention may a tablet-based computing device, a desktop computing device, or a workstation.

IMD 104, clinician programmer 110 and patient programmer 112 may, as shown in FIG. 1, communicate via wireless communication. Clinician programmer 110 and patient programmer 112 may, for example, communicate via wireless communication with IMD 104 using radio frequency (RF) telemetry techniques known in the art. Clinician programmer 110 and patient programmer 112 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 110 and patient programmer 112 need not communicate wirelessly, however. For example, programmers 110 and 112 may communicate via a wired connection, such as via a serial communication cable, or via exchange of removable media, such as magnetic or optical disks, or memory cards or sticks. Further, clinician programmer 110 may communicate with one or both of IMD 104 and patient programmer 112 via remote telemetry techniques known in the art, communicating via a local area network (LAN), wide area network (WAN), public switched telephone network (PSTN), or cellular telephone network, for example.

Figure 8:
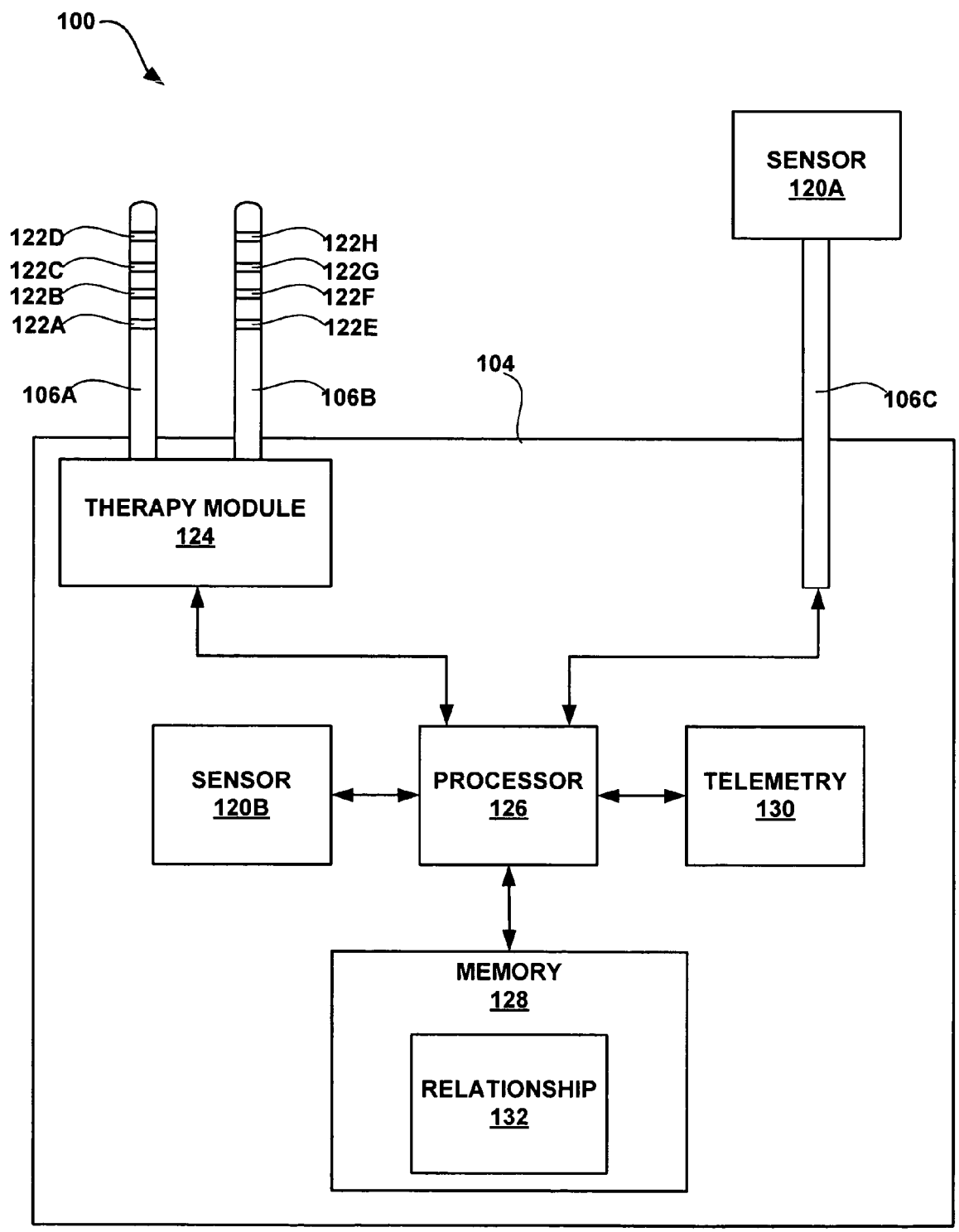
FIG. 8 is a block diagram further illustrating the system of FIG. 7.

FIG. 8 is a block diagram further illustrating system 100. In particular, FIG. 2 illustrates an example configuration of IMD 104 and leads 106A and 106B. FIG. 2 also illustrates sensors 120A and 120B (collectively "sensors 120") that output signals as a function of one or more physiological parameters of patient 12 that are part of the non-PSG physiological parameter set. Sensors 120 may include any of the non-PSG sensors 42 discussed above with reference to FIG. 2.

IMD 104 may deliver neurostimulation therapy via electrodes 122A-D of lead 106A and electrodes 122E-H of lead 106B (collectively "electrodes 122"). Electrodes 122 may be ring electrodes. The configuration, type and number of electrodes 122 illustrated in FIG. 8 are merely exemplary. For example, leads 106A and 106B may each include eight electrodes 122, and the electrodes need not be arranged linearly on each of leads 106A and 106B.

Electrodes 122 are electrically coupled to a therapy delivery module 124 via leads 106A and 106B. Therapy delivery module 124 may, for example, include an output pulse generator coupled to a power source such as a battery. Therapy delivery module 124 may deliver electrical pulses to patient 102 via at least some of electrodes 122 under the control of a processor 126, which controls therapy delivery module 124 to deliver neurostimulation therapy according to one or more neurostimulation therapy parameter sets selected from available parameter sets stored in a memory 128. However, the invention is not limited to implantable neurostimulator embodiments or even to IMDs that deliver electrical stimulation. For example, in some embodiments a therapy delivery module of an IMD may include a pump, circuitry to control the pump, and a reservoir to store a therapeutic agent for delivery via the pump, and a processor of the IMD may control delivery of a therapeutic agent by the pump according to an infusion parameter set selected from among a plurality of infusion parameter sets stored in a memory.

IMD 14 may also include a telemetry circuit 130 that enables processor 126 to communicate with programmers 110, 112. Via telemetry circuit 130, processor 126 may receive therapy parameter sets specified by a clinician from clinician programmer 110 for storage in memory 128. Processor 126 may also receive therapy parameter set selections and therapy adjustments made by patient 102 using patient programmer 112 via telemetry circuit 130. Further, processor 126 may receive a determined relationship 132 between values of the non-PSG physiological parameter set and sleep states from one of programmers 110, 112 via telemetry circuit 130, and store the relationship in memory 128, as shown in FIG. 8.

Processor 126 may include a microprocessor, a controller, a DSP, an ASIC, a FPGA, discrete logic circuitry, or the like. Memory 128 may include any volatile, non-volatile, magnetic, optical, or electrical media, such as a RAM, ROM, NVRAM, EEPROM, flash memory, or the like. In some embodiments, memory 128 stores program instructions that, when executed by processor 126, cause IMD 104 and processor 126 to perform the functions attributed to them herein.

Each of sensors 120 outputs a signal as a function of one or more physiological parameters of patient 102 within the non-PSG physiological parameter set. IMD 104 may include circuitry (not shown) that conditions the signals output by sensors 120 such that they may be analyzed by processor 126. For example, IMD 104 may include one or more analog to digital converters to convert analog signals output by sensors 120 into digital signals usable by processor 126, as well as suitable filter and amplifier circuitry. Although shown as including two sensors 120, system 100 may include any number of sensors.

Further, as illustrated in FIG. 8, sensors 120 may be included as part of IMD 104, or coupled to IMD 104 via leads 106. Sensors 120 may be coupled to IMD 104 via therapy leads 106A and 106B, or via other leads 106, such as lead 106C depicted in FIG. 8. In some embodiments, a sensor located outside of IMD 104 may be in wireless communication with processor 126. Wireless communication between sensors 120 and IMD 104 may, as examples, include RF communication or communication via electrical signals conducted through the tissue and/or fluid of patient 102.

Processor 126 may apply relationship 132 to non-PSG physiological parameter values determined based on signals received from sensors 120 to identify sleep states of patient 102. In other embodiments, processor 126 may provide the non-PSG physiological parameter values to one of programmers 110, 112, or another computing device, via telemetry circuitry 132. In such embodiments, the programmer or computing device stores relationship 132, and applies the relationship to the non-PSG parameter values to identify sleep states. One or more of processor 126, a programmer 110, 112, or another computing device may evaluate sleep quality or the efficacy of therapy delivered by IMD 104 based on the identified sleep states, or control therapy delivered by IMD 104 based on identified sleep states or determined sleep quality, as described above.

Further details regarding identification of sleep states, evaluating sleep quality using medical devices, and controlling therapy based on identified sleep states and/or sleep quality may be found in the following commonly-assigned applications, which are incorporated herein by reference in their entirety: (1) U.S. patent application Ser. No. 11/081,811, by Kenneth T. Heruth and Keith A. Miesel, entitled "Collecting Sleep Quality Information Via a Medical Device," filed Mar. 16, 2005; (2) U.S. patent application Ser. No. 11/081,872, by Kenneth T. Heruth and Keith A. Miesel, entitled "Collecting Posture Information to Evaluate Therapy," filed Mar. 16, 2005; (3) U.S. patent application Ser. No. 11/081,786, by Kenneth T. Heruth and Keith A. Miesel, entitled "Detecting Sleep," filed Mar. 16, 2005; (4) U.S. patent application Ser. No. 11/081,785, by Kenneth T. Heruth and Keith A. Miesel, entitled "Collecting Activity Information to Evaluate Therapy," filed Mar. 16, 2005; (5) U.S. patent application Ser. No. 11/081,857, by Kenneth T. Heruth and Keith A. Miesel, entitled "Collecting Activity and Sleep Quality Information via a Medical Device," filed Mar. 16, 2005; (6) U.S. patent application Ser. No. 11/081,155, by Kenneth T. Heruth and Keith A. Miesel, entitled "Controlling Therapy Based on Sleep Quality," filed Mar. 16, 2005; (7) U.S. patent application Ser. No. 11/081,873, by Kenneth T. Heruth and Keith A. Miesel, entitled "Sensitivity Analysis for Selecting Therapy Parameter Sets," filed Mar. 16, 2005; (8) U.S. patent application Ser. No. 11/106,051, by Keith A. Miesel, entitled "Collecting Posture and Activity Information to Evaluate Therapy," filed Apr. 14, 2005.

Various embodiments of the invention have been described. However, one skilled in the art will appreciate that various modifications may be made to the described embodiments without departing from the scope of the invention. For example, PSG and non-PSG physiological parameters are not limited to the examples cited herein, but may include any known PSG or non-PSG physiological parameters. Further, the invention is not limited to embodiments that include the example sensors cited herein. Instead, the invention may include any sensor known to generate a signal as a function of a physiological parameter.

Although described herein as a single computer, processor, and memory, the various functions attributed to computers, processors and memory herein may be performed at different time and locations by different processing, computing and memory devices. Consequently, as used herein, the terms "computer," "processor" and "memory" may respectively refer to: one or more computing devices, e.g., one or more personal computers, workstations, or network servers; one or more processing devices, e.g., one or more microprocessors, controllers, DSPs, ASICs, FPGAs, logic circuits, or the like; and one or more memory devices or media.

Further, although described herein as including separate non-PSG and PSG data recorders 26 and 30 that independently communicate with a computer 32 including a processor 34, systems 10 according to the invention are not so limited. For example, in some embodiments, a single data recorder may collect both the PSG and non-PSG physiological parameter values from PSG and non-PSG sensors 42 and 50. In other embodiments, one of recorders 26, 30 may transmit physiological parameter values to the other of recorders 26, 30, rather than computer 32, and the other of recorders 26, 30 may transmit both data collected from sensors and received from the recorder to computer 32. Further, in some embodiments, a processor of one of the data recorders, rather than processor 34 of computer 32, may correlate non-PSG physiological parameter values with sleep states and determine a relationship therebetween. In such embodiments, a system 10 need not include a computer 32. Additionally, if subjects 12 have a medical device, such as an IMD, which includes or is coupled to PSG or non-PSG sensors, a computer 32 or recorder 26, 30 may receive parameter values from the medical device sensors, rather than coupling redundant sensors to the subject.

Additionally, as described above, a relationship between non-PSG physiological parameter values and sleep states may be determined based on PSG and non-PSG data collected from a plurality of subjects. Such a relationship may be used in medical devices of any number of patients—who may be different from the experimental subjects—to identify sleep states of the patients. In other words, a "global" relationship between values of a non-PSG physiological parameter set and sleep states may be determined based on the data collected from a plurality of experimental subjects, and used in any medical device that includes or is coupled to sensors that sense physiological parameters of the non-PSG physiological parameter set to identify sleep states of any patient.

In other embodiments, values of the non-PSG physiological parameter set may be correlated to PSG-determined sleep states for a single patient, the correlated values of the non-PSG parameter set and sleep states for the single patient may be analyzed, and a relationship that allows determination of sleep states for the patient based on values of the non-PSG physiological parameter set for the patient may be developed based on the analysis. Such a relationship may be used by a medical device of that particular patient to determine sleep states. In such embodiments, the medical device includes or is coupled to non-PSG sensors, and may be used record values for the non-PSG physiological parameters, instead of a separate data recorder, during the period of data collection prior to determination of the relationship.

These and other embodiments are within the scope of the following claims.

The invention claimed is:

1. A method comprising:
   identifying sleep states of a subject during a period of time based on polysomnography;
   recording values of a non-polysomnographic physiological parameter set of the subject during the period of time;
   subsequent to identifying the sleep states and recording the values of the non-polysomnographic physiological parameter set, correlating the recorded values of the non-polysomnographic physiological parameter set to the identified sleep states using a computing device;
   subsequent to correlating the recorded values to the identified sleep states, analyzing the correlated values of the non-polysomnographic physiological parameter set using the computing device;
   subsequent to analyzing the correlated values, calculating a relationship between values of the non-polysomnographic physiological parameter set and sleep states based on the analysis using the computing device; and
   subsequent to calculating the relationship, storing the relationship between values of the non-polysomnographic physiological parameter set and sleep states in a medical device, wherein the medical device is configured to apply the relationship to a non-polysomnographic physiological parameter to identify sleep states based on the relationship.

2. The method of claim 1, wherein the non-polysomnographic physiological parameter set includes at least one of posture, activity level, heart rate, respiration rate, respiratory volume, blood oxygen saturation, blood pressure, electrocardiogram (ECG) morphology, core temperature, partial pressure of oxygen within blood, partial pressure of oxygen within cerebral spinal fluid, pH of blood or cerebral spinal fluid, glucose level in blood or cerebral spinal fluid, protein marker of pain within cerebral spinal fluid or subcutaneous extracellular fluid, muscular activity, muscular tone, arterial blood flow, or galvanic skin response.

3. The method of claim 1, wherein identifying sleep states of a subject comprises identifying whether the subject is awake or asleep.

4. The method of claim 1, wherein identifying sleep states of a subject comprises identifying whether the subject is in a random eye movement or non-random eye movement state of sleep.

5. The method of claim 1, wherein identifying sleep states of a subject comprises identifying whether the subject is in at least one of the S1, S2, S3 or S4 sleep state.

6. The method of claim 1, wherein identifying sleep states of a subject comprises:
recording values of a polysomnographic physiological parameter set of the subject during the period of time; and
analyzing the values of the polysomnographic physiological parameter set to identify the sleep states.

7. The method of claim 6, wherein recording values of a polysomnographic physiological parameter set and a non-polysomnographic physiological parameter set comprises recording values in a clinic during the period of time.

8. The method of claim 1, wherein recording values of a non-polysomnographic physiological parameter set comprises recording values of the non-polysomnographic physiological parameter set via at least one sensor located proximate to an implantable medical device implant location.

9. The method of claim 1,
further comprising identifying sleep states, recording values of a non-polysomnographic physiological parameter set, and, subsequent to identifying the sleep states and recording the values of the non-polysomnographic physiological parameter set, correlating the recorded values of the non-polysomnographic physiological parameter set to the identified sleep states for each of a plurality of subjects,
wherein analyzing the correlated values comprises, subsequent to correlating the recorded values to the identified sleep states, analyzing the correlated values for the plurality of subjects, and calculating a relationship comprises, subsequent to analyzing the correlated values, calculating the relationship based on the analysis for the plurality of subjects.

10. The method of claim 9, wherein the plurality of subjects comprises a first plurality of subjects, the method further comprising:
for each of a second plurality of subjects, identifying sleep states during a period of time based on polysomnography, recording values of a non-polysomnographic physiological parameter set during the period of time, and, subsequent to recording the values, applying the relationship to the recorded values to identify sleep states during the period of time;
subsequent to applying the relationship, comparing the identification of sleep states based on polysomnography to the identification of sleep states by application of the relationship; and
subsequent to comparing the identifications, modifying the relationship based on the comparison.

11. The method of claim 1, wherein calculating a relationship comprises calculating at least one of a threshold, an equation, a look-up table, or a neural network.

12. The method of claim 1, further comprising:
recording values of the non-polysomnographic physiological parameter set for a patient via the medical device;
subsequent to recording the values, applying the relationship to the values of the non-polysomnographic physiological parameter set; and
subsequent to applying the relationship to the values, identifying sleep states of the patient based on the application of the relationship.

13. The method of claim 1, wherein the medical device is an implantable medical device.

14. The method of claim 12, further comprising:
evaluating quality of sleep of the patient based on the identified sleep states; and
evaluating efficacy of therapy delivered to the patient by the medical device based on the quality of sleep.

15. The method of claim 12, further comprising controlling delivery of therapy by the medical device based on the identified sleep states.

16. A system comprising
a first plurality of sensors that sense a polysomnographic physiological parameter set of a subject;
a second plurality of sensors that sense a non-polysomnographic physiological parameter set of the subject;
a processor that receives signals sensed by the first and second pluralities of sensors during a period of time, determines values of the polysomnographic physiological parameter set and the non-polysomnographic physiological parameter set based on the signals, identifies sleep states based on values of the polysomnographic physiological parameter set, subsequent to determining the values of the non-polysomnographic physiological parameter set and identifying the sleep states, correlates the values of the non-polysomnographic physiological parameter set with sleep states identified based on values of the polysomnographic physiological parameter set, subsequent to correlating the recorded values to the identified sleep states, analyzes the correlated values of the non-polysomnographic physiological parameter set, and, subsequent to analyzing the correlated values, calculates a relationship that relates values of the non-polysomnographic physiological parameter set to sleep states based on the analysis; and
a medical device comprising a memory that, subsequent to the processor calculating the relationship, stores the relationship between values of the non-polysomnographic physiological parameter set and sleep states, wherein the medical device is configured to apply the relationship to a non-polysomnographic physiological parameter to identify sleep states based on the relationship.

17. The system of claim 16, wherein the processor presents the values of the polysomnographic physiological parameter set to a user for identification of sleep states of the subject, subsequent to presenting the values, receives an indication of the sleep states from the user, identifies sleep states based on the indication, and, subsequent to identifying the sleep states, correlates the values of the non-polysomnographic physiological parameter set with the identified sleep states.

18. The system of claim 16, wherein the processor analyzes the values of the polysomnographic physiological parameter set, identifies sleep states of the subject based on the analysis, and, subsequent to identifying the sleep states, correlates the values of the non-polysomnographic physiological parameter set with the identified sleep states.

19. The system of claim 16, wherein the processor, subsequent to correlating the recorded values to the identified sleep states, presents the correlated values of non-polysomnographic physiological parameter set and sleep states to a user.

20. The system of claim 16,
wherein the processor receives signals, determines values of the polysomnographic physiological parameter set and the non-polysomnographic physiological parameter set, identifies sleep states based on values of the polysomnographic physiological parameter set and, subsequent to determining the values of the non-polysomnographic physiological parameter set and identifying the sleep states, correlates the values of non-polysomnographic physiological parameter set with sleep states identified based on the values of the polysomnographic physiological parameter set for each of a plurality of subjects, and wherein the processor, subsequent to correlating the recorded values to the identified sleep states, analyzes the correlated values for the plurality of subjects, and, subsequent to analyzing the correlated values, calculates the relationship based on the analysis for the plurality of subjects.

21. The system of claim 20, wherein the plurality of subjects comprises a first plurality of subjects, and, for each of a second plurality of subjects, the processor identifies sleep states during a period of time based on polysomnography, records values of a non-polysomnographic physiological parameter set during the period of time, and, subsequent to recording the values of the non-polysomnographic physiological parameter set, applies the relationship to the recorded values to identify sleep states during the period of time, and wherein the processor, subsequent to applying the relationship, compares the identification of sleep states based on polysomnography to the identification of sleep states by application of the relationship, and, subsequent to comparing the identifications, modifies the relationship based on the comparison.

22. The system of claim 16, wherein the relationship comprises at least one of a threshold, an equation, a look-up table, or a neural network.

23. The system of claim 16, wherein first plurality of sensors include at least one of sensors that sense brain electrical activity, sensors that sense eye motion, or sensors that sense jaw or neck muscle activity or tension.

24. The system of claim 16, wherein the second plurality of sensors includes at least one of sensors that sense posture, sensors that sense activity level, sensors that sense heart rate, sensors that sense respiration rate, sensors that sense respiratory volume, sensors that sense blood oxygen saturation, sensors that sense blood pressure, sensors that sense electrocardiogram (ECG) morphology, sensors that sense core temperature, sensors that sense partial pressure of oxygen within blood, sensors that sense partial pressure of oxygen within cerebral spinal fluid, sensors that sense pH of blood or cerebral spinal fluid, sensors that sense glucose level in blood or cerebral spinal fluid, sensors that sense protein marker of pain within cerebral spinal fluid or subcutaneous extracellular fluid, sensors that sense muscular activity, sensors that sense muscular tone, sensors that sense arterial blood flow, or sensors that sense galvanic skin response.

25. The system of claim 16, wherein at least one of the second plurality of sensors is located proximate to an implantable medical device implant location.

26. The system of claim 16, further comprising an external data recorder that receives signals from the second plurality of sensors, and provides the received signals to the processor.

27. The system of claim 26, wherein the period of time is a first period of time, the external data recorder receives signals from the sensors during the first period of time, stores the signals in a memory, and provides the stored signals to the processor during a second period of time.

28. The system of claim 27, further comprising a device that includes the processor, wherein the memory is a removable memory that is receivable by the device that includes the processor for provision of the stored signals to the processor.

29. The system of claim 26, wherein the external data recorder is configured to be worn by the subject, includes a housing, and includes at least one of the second plurality of sensors within the housing.

30. The system of claim 29, wherein the external data recorder includes a three-axis accelerometer.

31. The system of claim 26, wherein the external data recorder comprises first external data recorder, the system further comprising a second external data recorder that receives signals from the first plurality of sensors, and provides the received signals to the processor.

32. The system of claim 16, further comprising a computer that includes the processor.

33. A system comprising:
means for identifying sleep states of a subject during a period of time based on polysomnography;
means for recording values of a non-polysomnographic physiological parameter set of the subject during the period of time;
means for correlating the recorded values of the non-polysomnographic physiological parameter set to the sleep states identified by polysomnography during the period of time subsequent to identifying the sleep states and recording the values of the non-polysomnographic physiological parameter set;
means for analyzing the correlated values of the non-polysomnographic physiological parameter set subsequent to correlating the recorded values to the identified sleep states;
means for calculating a relationship between values of the non-polysomnographic physiological parameter set and sleep states based on the analysis subsequent to analyzing the correlated values; and
means for storing the relationship between values of the non-polysomnographic physiological parameter set and sleep states in a medical device to determining the relationship wherein the medical device is configured to apply the relationship to a non-polysomnographic physiological parameter to identify sleep states based on the relationship.

34. The system of claim 33, wherein the means for identifying sleep states comprises means for identifying sleep states for each of a plurality of subjects during respective periods of time, the means for recording comprises means for recording values of the non-polysomnographic physiological parameter set for each of the plurality of subjects during the respective periods of time, the means for correlating comprises means for correlating the values of the non-polysomnographic physiological parameter set recorded during the respective periods of time for each of the subjects to the sleep states identified by polysomnography during the respective periods of time for each of the subjects subsequent to identifying the sleep states and recording the values of the non-polysomnographic physiological parameter set during the respective periods of time for each of the subjects, the means for analyzing comprises means for analyzing the correlated values for each of the plurality of subjects subsequent to correlating the recorded values to the identified sleep states for each of the subjects, and the means for calculating a relationship comprises means for calculating the relationship based on the analysis for the plurality of subjects subsequent to analyzing the correlated values for each of the subjects.

35. A non-transitory computer-readable medium comprising instructions that cause a programmable processor to:
identify sleep states of a subject during a period of time based on polysomnography;

record values of a non-polysomnographic physiological parameter set of the subject during a period of time;

subsequent to identifying the sleep states and recording the values of the non-polysomnographic physiological parameter set, correlate the recorded values of the non-polysomnographic physiological parameter set to the sleep states identified by polysomnography during the period of time;

subsequent to correlating the recorded values to the identified sleep states, analyze the correlated values of the non-polysomnographic physiological parameter set;

subsequent to analyzing the correlated values, calculate a relationship that relates values of the non-polysomnographic physiological parameter set to sleep states based on the analysis; and subsequent to calculating the relationship, store the relationship between values of the non-polysomnographic physiological parameter set and sleep states in a medical device, wherein the medical device is configured to apply the relationship to a non polysomnographic physiological parameter to identify sleep states based on the relationship.

36. The non-transitory computer-readable medium of claim 35, wherein the instructions that cause a programmable processor to identify sleep states, record values of a non-polysomnographic physiological parameter set, and correlate the recorded values to the sleep states comprise instructions that cause a programmable processor to identify sleep states, record values of the non-polysomnographic physiological parameter set, and, subsequent to identifying the sleep states and recording the values of the non-polysomnographic physiological parameter set, correlate the recorded values to the sleep states for each of a plurality of subjects, and wherein the instructions that cause a programmable processor to analyze the correlated values and calculate a relationship based on the analysis comprise instructions that cause a programmable processor to, subsequent to correlating the recorded values to the identified sleep states, analyze the correlated values for the plurality of subjects and calculate the relationship based on the analysis.

* * * * *